(12) United States Patent
Ilios et al.

(10) Patent No.: US 10,039,670 B2
(45) Date of Patent: Aug. 7, 2018

(54) FERROMAGNETIC VALVES

(71) Applicant: Massachusetts Eye & Ear Infirmary, Boston, MA (US)

(72) Inventors: Eleftherios Paschalis Ilios, Cambridge, MA (US); Claes H. Dohlman, Weston, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 586 days.

(21) Appl. No.: 14/423,635

(22) PCT Filed: Aug. 30, 2013

(86) PCT No.: PCT/US2013/057577
§ 371 (c)(1),
(2) Date: Feb. 24, 2015

(87) PCT Pub. No.: WO2014/036437
PCT Pub. Date: Mar. 6, 2014

(65) Prior Publication Data
US 2015/0202082 A1    Jul. 23, 2015

Related U.S. Application Data

(66) Substitute for application No. 61/695,150, filed on Aug. 30, 2012.

(51) Int. Cl.
*A61M 5/00*  (2006.01)
*A61F 9/007*  (2006.01)
(Continued)

(52) U.S. Cl.
CPC ....... *A61F 9/00781* (2013.01); *A61M 39/228* (2013.01); *F16K 99/0046* (2013.01);
(Continued)

(58) Field of Classification Search
CPC ........ A61F 9/00781; A61F 2250/0013; A61M 39/228; A61M 2205/0272; A61M 2205/0288; F16F 99/0046
See application file for complete search history.

(56) References Cited

U.S. PATENT DOCUMENTS 4,478,424 A    10/1984  Raj
7,947,008 B2    5/2011  Grahn et al.
(Continued)

FOREIGN PATENT DOCUMENTS

WO    2004/073564    9/2004

OTHER PUBLICATIONS

Hartshorne et al., "Ferrofluid-based microchip pump and valve," Sensors and Actuators, 99:592-600 (Jan. 2004).
(Continued)

*Primary Examiner* — Philip R Wiest
(74) *Attorney, Agent, or Firm* — Fish & Richardson P.C.

(57) ABSTRACT

The disclosure includes devices and methods for controlling fluid flow. The devices include a tube configured to receive fluid from a fluid source; and a valve for controlling fluid flow through the tube, the valve responsive to fluid pressure in the tube. The valve includes a first magnet outside the tube at a fixed first distance from the tube and a second magnet outside the tube substantially opposite the first magnet and at a second distance from the tube, the second distance greater than the first distance. The valve includes a ferromagnetic fluid within the tube between the first magnet and the second magnet and held in position by a magnetic field generated by the first magnet. The amount of ferromagnetic fluid is sufficient to seal the tube when the fluid pressure is below a threshold pressure set by the second distance between the second magnet and the tube.

34 Claims, 19 Drawing Sheets

(51) Int. Cl.
  *A61M 39/22* (2006.01)
  *F16K 99/00* (2006.01)
(52) U.S. Cl.
  CPC ............... *A61F 2250/0013* (2013.01); *A61M 2205/0272* (2013.01); *A61M 2205/0288* (2013.01); *A61M 2210/0612* (2013.01)

(56) References Cited

U.S. PATENT DOCUMENTS

| | | |
|---|---|---|
| 8,167,265 B2 | 5/2012 | Oh et al. |
| 2007/0283960 A1 | 12/2007 | Meckes et al. |
| 2009/0131959 A1* | 5/2009 | Rolland ............... A61F 2/04 606/158 |
| 2009/0275924 A1* | 11/2009 | Lattanzio ............. A61B 3/16 604/891.1 |

OTHER PUBLICATIONS

International Search Report and Written Opinion issued in PCT/US2013/057577 dated Nov. 27, 2013 (14 pages).

* cited by examiner

FERROMAGNETIC VALVES

CLAIM OF PRIORITY

This application is a 371 U.S. National Application of PCT/US2013/057577, filed Aug. 30, 2013, and claims priority to U.S. Provisional Application Ser. No. 61/695,150, filed on Aug. 30, 2012, the entire contents of which are hereby incorporated by reference.

FIELD OF THE INVENTION

The invention relates to ferromagnetic valves, e.g., for use in the eye.

BACKGROUND OF THE INVENTION

A ferromagnetic fluid is a liquid that becomes magnetized in the presence of a magnetic field. Ferromagnetic fluids can be used as passive components, such as seals, in which a ferromagnetic fluid is held in a fixed position by its attraction to a magnet. Ferromagnetic fluids can also be used as active components, such as valves, in which the ferromagnetic fluid changes position or configuration to open and close the valve controlled by an attraction between the ferromagnetic fluid and a magnet.

SUMMARY OF THE INVENTION

The invention is based, at least in part, on the discovery that a ferromagnetic valve including a ferromagnetic material (such as a ferromagnetic fluid, hereinafter also referred to as a "ferrofluid," or a ferromagnetic membrane) positioned in a tube between two magnets can control fluid flow through the tube responsive to a fluid pressure in the tube. In particular, when the fluid pressure in the tube is less than a threshold pressure, the ferromagnetic material seals the tube, thus closing the valve. When the fluid pressure is greater than a threshold pressure, the fluid pressure upstream of the valve pushes the ferromagnetic material aside to adopt a configuration that opens the valve, allowing the fluid to flow through the valve. The ferromagnetic valve is operable at low pressures and is useful for medical applications, such as for relieving high intraocular pressure associated with glaucoma.

In a general aspect, the disclosure features devices for controlling fluid flow that include a tube configured to receive fluid from a fluid source; and a valve for controlling fluid flow through the tube. The valve is responsive to a fluid pressure in the tube. The valve includes a first magnet disposed outside the tube and at a fixed first distance from the tube and a second magnet disposed outside the tube substantially opposite the first magnet and at a second distance from the tube. The second distance is greater than the first distance. The valve further includes a ferromagnetic fluid disposed within the tube between the first magnet and the second magnet and held in position by a magnetic field generated by at least the first magnet. The ferromagnetic fluid is present in an amount sufficient to seal the tube when the fluid pressure is below a threshold pressure set by the second distance between the second magnet and the tube.

Various embodiments and implementations of the invention can include one or more of the following features.

The tube can be configured to receive fluid from an eye of a patient. The valve can be configured to open when the fluid pressure in the tube increases beyond an opening threshold fluid pressure. The opening threshold fluid pressure can be a pressure sufficient to overcome a strength of a magnetic field generated by one or both of the first magnet and the second magnet. The opening threshold fluid pressure can be about 10 mm Hg, e.g., about 8, 9, 10, 11, or 12 mm Hg.

The valve can be configured to close when the fluid pressure in the tube decreases below a closing threshold fluid pressure. The closing threshold fluid pressure can be about 7 mm Hg, e.g., about 5, 6, 7, 8, or 9 mm Hg. The second magnet can be disposed at a fixed second distance from the tube. The valve can further include a channel disposed between the second magnet and the tube, and wherein the width of the channel is adjustable. The second magnet can be an electromagnet and the tube can be formed of quartz.

In some implementations, the tube can include a first region formed of a flexible material and configured to receive fluid from the eye; and a second region adjacent to the first region and formed of a rigid material. The valve can be disposed in the rigid region of the tube. The first region can be formed of rubber or silicone and the second region can be formed of quartz or PDMS of higher stiffness. The first magnet can be in contact with the tube.

The ferromagnetic fluid can include ferromagnetic particles disposed in a carrier fluid, wherein the carrier fluid is immiscible with water. In certain implementations, the carrier fluid is a fluorinated hydrocarbon. The ferromagnetic fluid can be contained within a membrane. The membrane can be formed in-situ. A separation between the first magnet and the tube can be less than a separation between the second magnet and the tube.

In another general aspect, the disclosure features methods for controlling fluid flow. These methods include receiving fluid from a fluid source into a tube; and controlling fluid flow through the tube using a valve responsive to a fluid pressure in the tube. The valve includes a ferromagnetic fluid disposed within the tube between a first magnet and a second magnet and held in position by a magnetic field generated by at least the first magnet.

Various embodiments and implementations of these methods can include one or more of the following features.

Receiving fluid can include receiving fluid from an eye of a patient into the tube. Controlling fluid flow can include causing the valve to close when the fluid pressure in the tube is less than a threshold fluid pressure. When the fluid pressure in the tube is less than the threshold fluid pressure, a strength of a magnetic field generated by the second magnet can be sufficient to hold the ferromagnetic fluid in a position that blocks fluid flow through the tube.

Controlling fluid flow can include causing the valve to open when the pressure difference increases beyond an opening threshold pressure difference. Controlling fluid flow can also include causing the valve to open when the fluid pressure in the tube increases beyond an opening threshold fluid pressure. The opening threshold pressure difference can be a pressure sufficient to overcome a strength of a magnetic field generated by the second magnet.

Controlling fluid flow can include causing the valve to close when the pressure difference decreases beyond a closing threshold fluid pressure. Controlling fluid flow can also include adjusting a distance between the second magnet and the tube.

In some implementations, the second magnet can be an electromagnet, and controlling fluid flow can include adjusting a strength of the electromagnet.

In another general aspect, the disclosure features devices for controlling fluid flow. The devices include a tube configured to receive fluid from a fluid source; and a valve, disposed along the tube, for controlling fluid flow through the tube. The valve is responsive to a fluid pressure in the tube. The valve includes a valve member including ferromagnetic particles, and a magnet disposed outside the tube and configured to apply a magnetic field to the membrane structure. The valve member is held in a configuration that seals the tube by the magnetic field generated by the magnet when the fluid pressure is below a threshold pressure.

Various embodiments and implementations of these devices can include one or more of the following features.

The valve can be disposed at an end of the tube. The valve member can include: a membrane, and a ferromagnetic fluid contained within the membrane. The valve member can include a membrane at least partially coated in a layer of ferromagnetic particles. The valve member can include magnetic nanoparticles homogeneously distributed across the area and through the thickness of the membrane. The valve member can be positioned to cover an end of the tube when the fluid pressure in the tube is less than a threshold fluid pressure. The valve member can also be configured to bend to cover the end of the tube when the fluid pressure is less than the threshold fluid pressure.

In some implementations, at least one edge of the valve member can be fixed in position. The magnet can be a ring-shaped magnet that is axially magnetized.

In another general aspect, the disclosure features methods for treating glaucoma including a step of positioning a device in an eye of subject, e.g., a human or animal subject, diagnosed with glaucoma. The device can be one described herein, and can include a tube configured to receive fluid from the eye, and a valve responsive to a fluid pressure in the tube. The fluid pressure in the tube is related to a fluid pressure in the eye. The valve includes a ferromagnetic fluid disposed within the tube between a first magnet and a second magnet and held in position by a magnetic field generated by at least the first magnet. The methods further include regulating the fluid pressure in the eye by controlling fluid flow through the tube using the valve.

The terms "ferromagnetic fluid" and "ferrofluid" as used herein refer to a solution or suspension of ferromagnetic particles in a carrier fluid. In general, the carrier fluid is selected to be immiscible with the fluid that is to pass through a ferromagnetic fluid valve including the ferrofluid. For example, if the fluid that is to pass through the valve is an aqueous liquid, such as certain bodily fluids, then the carrier fluid is a non-polar or hydrophobic fluid, e.g., an oil or fluorocarbon. If the fluid that is to pass through the valve is an oil or other non-polar liquid, then the ferrofluid carrier is an aqueous fluid. If the fluid that is to pass through the valve is a gas, then the carrier fluid is sufficiently viscous to hold the ferrofluid in a closed position given the appropriate magnetic strength and arrangement outside the tube.

The devices and methods described herein have numerous advantages. For instance, the ferromagnetic fluid valve systems include a pressure responsive valve that is operable at low pressures and for a small difference between opening and closing pressures. The operable pressure range of the valves renders the valve systems well suited for the treatment of high intraocular pressure associated with glaucoma. Furthermore, the pressure responsive nature of the valves allows high intraocular pressure to be relieved by drainage of fluid through the valves while avoiding excess drainage when the intraocular pressure returns to a normal level. The valve systems can be easily inserted into and removed from behind the lower eyelid of the eye without invasive or complex surgical procedures other than inserting a tiny catheter into the eye, thus enabling straightforward use and replacement of the valve system. The ferromagnetic fluid valve systems described herein can also be useful in treating other medical conditions, such as high intracranial pressure resulting from brain injury or a brain tumor, and in other microfluidic applications in which a pressure responsive valve operable at low pressures is relevant.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

The ferromagnetic valves described herein include a ferromagnetic material, e.g., a ferromagnetic fluid or a ferromagnetic membrane, positioned in a tube between two magnets. Together these components are arranged to control fluid flow through the tube responsive to a fluid pressure in the tube. In particular, when the fluid pressure in the tube is less than a threshold pressure, e.g., a closing threshold pressure, the ferromagnetic material seals the tube, thus closing the valve. When the fluid pressure is greater than a threshold pressure, e.g., an opening threshold pressure, the fluid pressure upstream of the valve pushes the ferromagnetic material aside to adopt a configuration that opens the valve, allowing the fluid to flow through the valve. The ferromagnetic valves are operable at low pressures and are thus useful for medical applications, such as for relieving high intraocular pressure associated with glaucoma, and for relieving other pressures within the body, e.g., intracranial pressure.

Figure 1:
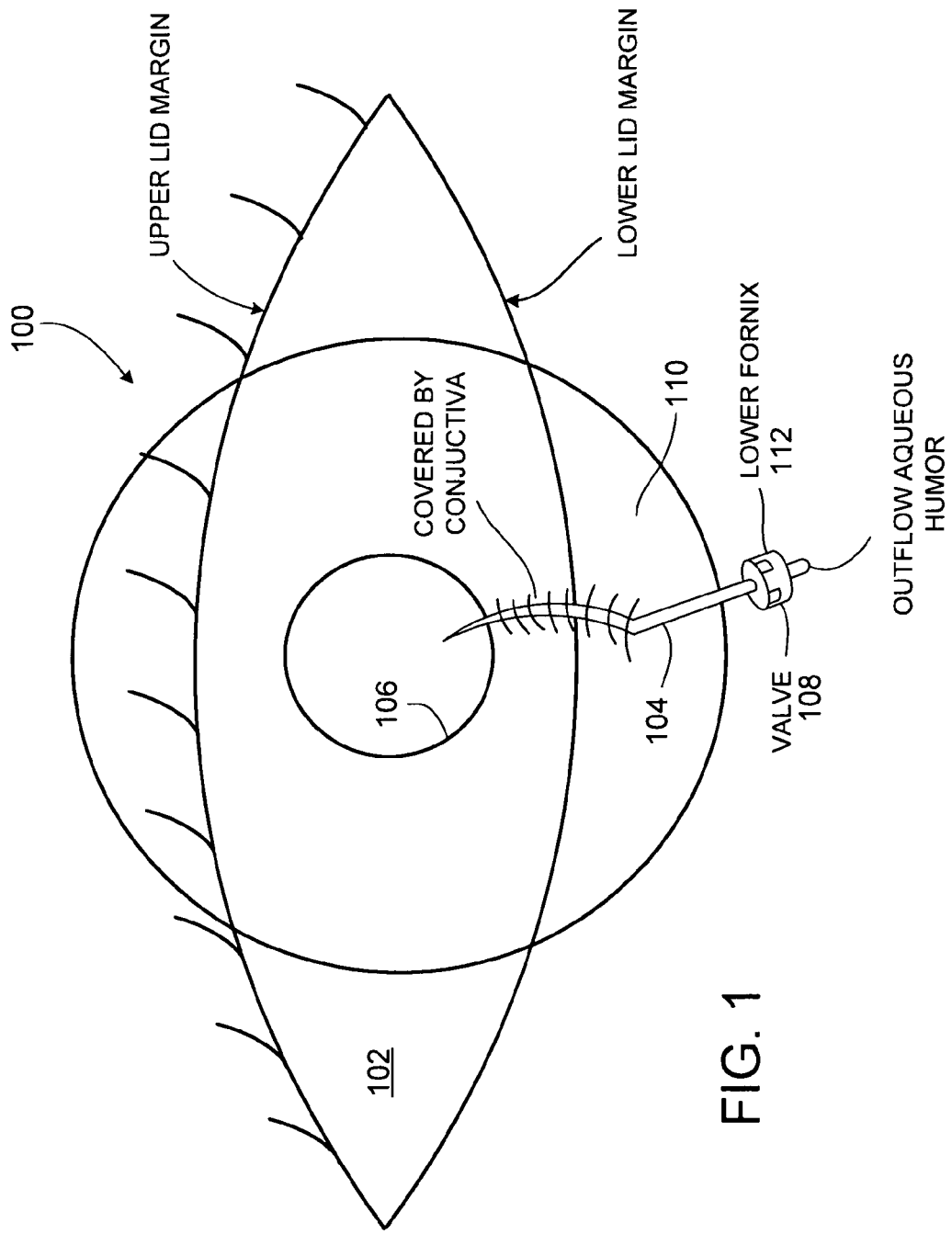
FIG. 1 is a schematic diagram of an eye into which a ferromagnetic fluid valve system has been inserted behind the lower eyelid.

FIG. 1 shows an example of a magnetic valve system 100 inserted behind the lower eyelid of an eye 102 to provide drainage of fluid, such as aqueous humor, from the eye. A tube 104 that is connected upstream of the valve 108 is inserted into the eye at the corneal limbus 106 to allow aqueous humor to flow out of the eye. At the opposite end of the tube 104, a ferromagnetic fluid valve 108 opens or closes to allow or restrict fluid outflow from the tube. The valve 108 is responsive to the fluid pressure within the tube 104, which corresponds to the intraocular pressure (IOP) in the eye. When the pressure in the tube (and hence the IOP) is low, the valve 108 remains closed and fluid flow is not permitted. When the IOP increases beyond a threshold level, the pressure in the tube 104 causes the valve 108 to open, thus allowing fluid to be drained from the eye. The valve system 100 is positioned under the conjunctiva 110. In some examples, the valve 108 is located at or near the end of the tube 104 and rests in the lower lid fornix 112.

As discussed in more detail below, the valve 108 operates based on a magnetic interaction between one or more fixed magnets and a moveable magnetic material, such as a ferrofluid. When the fluid pressure in the tube 104 is low, the attraction between the magnetic material and the fixed magnets causes the magnetic material to adopt a configuration that blocks the tube, thus closing the valve 108. However, a sufficiently high fluid pressure is able to overcome the magnetic attraction between the magnetic material and the fixed magnets, causing the magnetic material to move away from one or more of the fixed magnets and open a passage through the tube 104.

In some examples, the valve system 100 is used in treating glaucoma. Glaucoma patients suffer from high IOP resulting from an inability to effectively drain aqueous humor from the eye. Inserting the valve system 100 of a glaucoma patient can reduce the IOP by allowing aqueous humor to drain from the eye when the IOP exceeds a certain level. Because the valve 108 closes at low pressure, the valve system also prevents too much fluid from being drained from the eye, which could potentially result in hypotony (low IOP) and ultimately retinal detachment and/or choroidal hemorrhage.

The normal pressure in a healthy human eye is about 15.5 mm Hg. In one example, the valve 108 is designed to open when the IOP increases beyond about 10 mm Hg and to close when the IOP decreases below about 7 mm Hg to normalize the IOP in a glaucoma patient to a pressure below the normal IOP, thus alleviating mechanical stress on the optic nerve and thus providing maximum nerve damage reduction. The valve can be calibrated to operate at desired opening and closing pressures (e.g., at pressures equal to or less than about 30 mm Hg) by either changing the strength of the magnetic interaction between the ferrofluid and one or more of the fixed magnets or by using a larger volume of ferrofluid in the tube.

The ferromagnetic fluid valve systems described herein can also be used to relieve pressure buildup elsewhere in the body, e.g., to relieve intracranial pressure resulting from a brain injury or brain tumor. More generally, the magnetic valve systems described herein can be used in microfluidic applications in which a pressure responsive valve operable at low fluid pressures is relevant. For instance, the magnetic valve system can also be used for, e.g., microfluidic devices for biological sample testing, cell detection, PCR, DNA sequencing, flow cytometry, cell sorting, lab-on-a-chip applications, droplet generation, and other applications.

Structure of the Ferromagnetic Fluid Valves

Figure 2A:
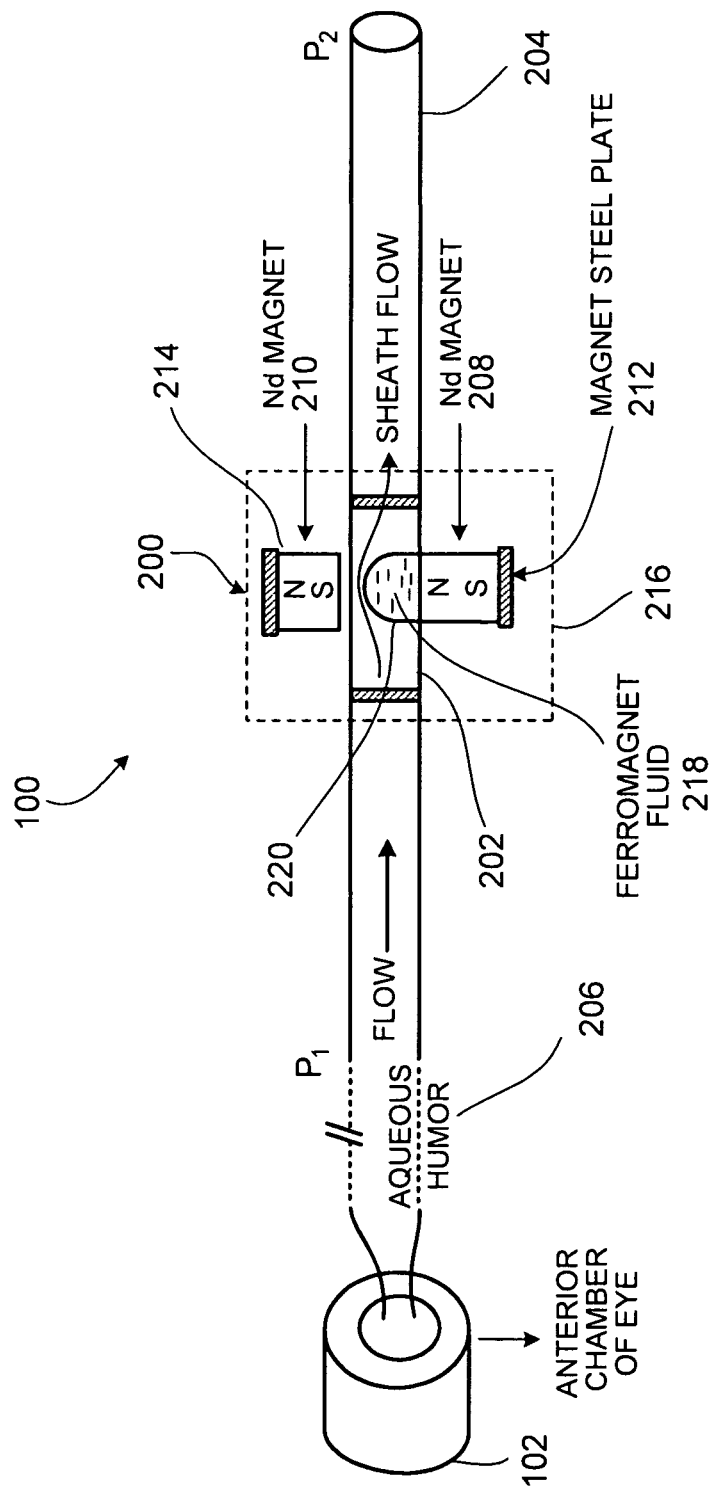
FIG. 2A is a schematic diagram of one example of a ferromagnetic fluid valve.
Figure 2B:
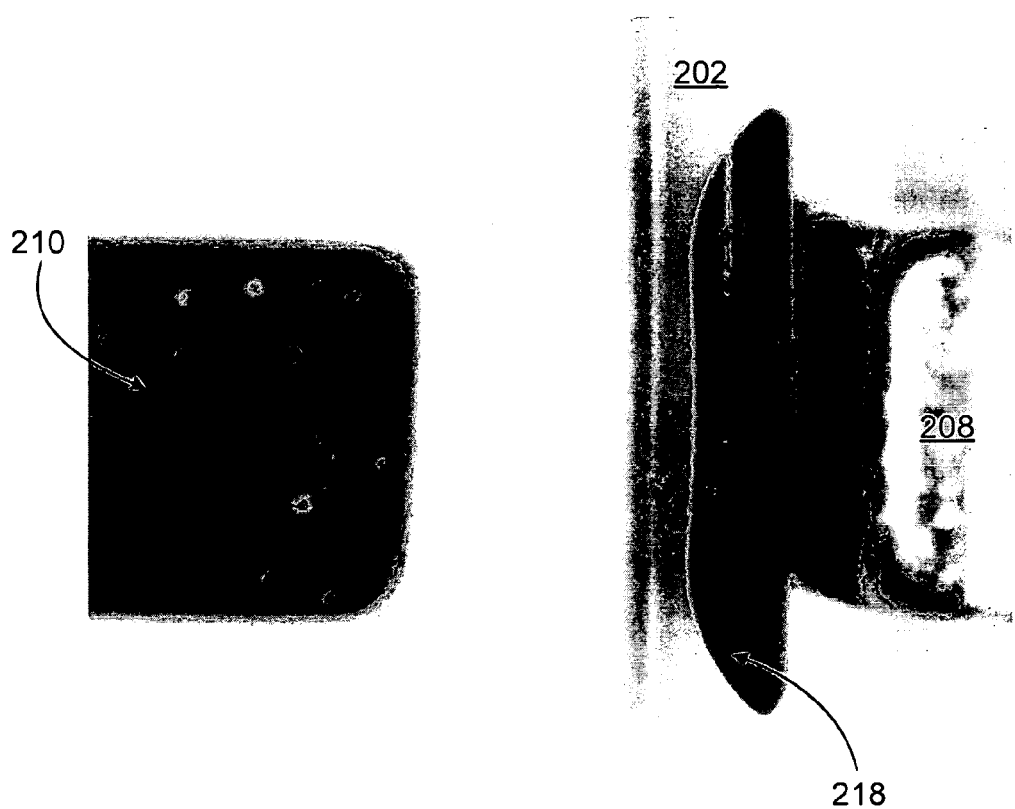
FIG. 2B is an optical microscope photograph of an example of a ferromagnetic fluid valve.

FIGS. 2A and 2B illustrate one example of a ferromagnetic fluid valve 200 that forms part of the magnetic system 100. The valve 200 is positioned on a tube subsection 202 located, e.g., toward a proximal end 204 of the tube 104. In other examples, the valve is positioned at other locations along the tube 104. A distal end 206 of the tube 104 is placed in a location appropriate to receive fluid from the eye 102.

The tube 104 is generally formed of an inert, flexible material, such as rubber or silicone (and is typically sterile before insertion into the eye). The tube subsection 202 is formed of a rigid, inert, non-magnetizable material, such as quartz, glass, or ceramic. Alternatively, the tube subsection is formed of a flexible silicone-based polymeric channel (e.g., polydimethylsiloxane (PDMS)) with a surface treatment to change the surface energy of the tube (e.g., a surface treatment to form a hydrophobic, hydrophilic, oleophobic, or oleophilic surface). In some examples, other portions of the tube 104 are also formed of the same material as the tube subsection 202. For instance, with appropriate surface modification, both the tube 104 and the tube subsection 202 may be formed of a single polymeric material, such as PDMS or silicone.

A first magnet 208 is positioned on a first side of the tube subsection 202 and at a first distance from the tube. In some examples, the first magnet is in contact with the tube. A second magnet 210 is positioned opposite the first magnet 208 and at a greater distance from the tube than the first distance, e.g., at a distance of about 100-300 μm from the tube. In some examples, the magnets are square magnets, such as 1/16" square magnets. In other examples, the magnets are circular magnets have a diameter of about 300-400 μm. More generally, the size of the magnets is determined based on the size of the tube; the volume, viscosity, and magnetic properties of a ferrofluid contained within the tube (discussed in greater detail below), and the target pressures for opening and closing the valve.

The magnets can be permanent magnets, such as neodymium magnets formed of an alloy of neodymium, iron, and boron (e.g., $Nd_2Fe_{14}B$). In some examples, the surface field of the magnets is about 5700 Gauss. The polarities of the magnets are inverted such that, for instance, the North pole of the first magnet 208 and the South pole of the second magnet 210 are the closest to the tube, thus providing bidirectional magnetic attraction to the ferrofluid. In some embodiments, the magnets can also be electromagnets, such as spiral printed coils, where a current flow in the coils generates a magnetic flux that changes according to the polarity of the biased current. The coils may be fabricated, e.g., using sputtering techniques, electron beam etching, chemical wet or dry etching techniques or soft lithography molding by filling micro-channels with liquid metal.

In some implementations, the first and second magnets are enclosed within a protective housing 216 formed of an inert plastic or polymer, e.g., polydimethylsiloxane (PDMS), Delrin®, silicon, poly(methyl methacrylate (PMMA), epoxy, polyamide, parylene, or another plastic. In some implementations (e.g., for experimental uses), the first and second magnets 208, 210 are mounted on support plates 212, 214, respectively, such as magnetic steel plates. In one example, the magnets 208, 210 are mounted on the support plates 212, 214 via a magnetic interaction. In another example, the magnets 208, 210 are mechanically affixed to the support plates 212, 214, e.g., with screws or bolts. The support plates 212, 214 can be connected directly to the tube 104 or can be connected to the housing 216.

A small volume of ferrofluid 218 (e.g., a fraction of a microliter, and depending on the diameter of the tube), is positioned within the tube subsection 202 between the first magnet 208 and the second magnet 210. The ferrofluid is a solution or suspension of ferromagnetic particles in a carrier fluid selected to be immiscible with the fluid that is to pass through a ferromagnetic fluid valve including the ferrofluid. In one example, the ferrofluid 218 includes a suspension of surfactant-coated ferrite nanoparticles in a hydrocarbon or fluorocarbon carrier fluid. For instance, the carrier fluid can be perfluoroalkylpolyether (PFPE). In some cases, the ferrofluid 218 forms a "droplet" separated from the fluid flowing through the tube 104 by a meniscus.

In some examples, the second magnet 210 is positioned slightly closer to the eye than the first magnet 208 (i.e., opposite the distal end 204 of the tube 104). When a fluid in the tube exerts pressure on the ferrofluid 218 (discussed in greater detail below), the ferrofluid 218 bends downstream due to the fluid flow. The second magnet 210, which controls the opening and closing of the valve, is placed upstream to compensate for the bending of the ferrofluid 218.

In some implementations, the ferrofluid 218 is contained within a flexible membrane 220, such as a PDMS or silicone membrane or other elastic polymer. The membrane 220 may be attached to the tube via a mechanical connection or chemical interaction as described above. The membrane 220 eliminates interactions between the ferrofluid and the liquid flowing through the tube. In one example, the membrane 220 is prepared in situ by flowing PDMS through the tube to form a coating the internal surfaces of the tube, including the surface of the ferrofluid. The PDMS coating is cured under continuous air or liquid flow through the channel at high temperatures (e.g., 65-95° C.) to form the membrane 220.

Figure 3A:
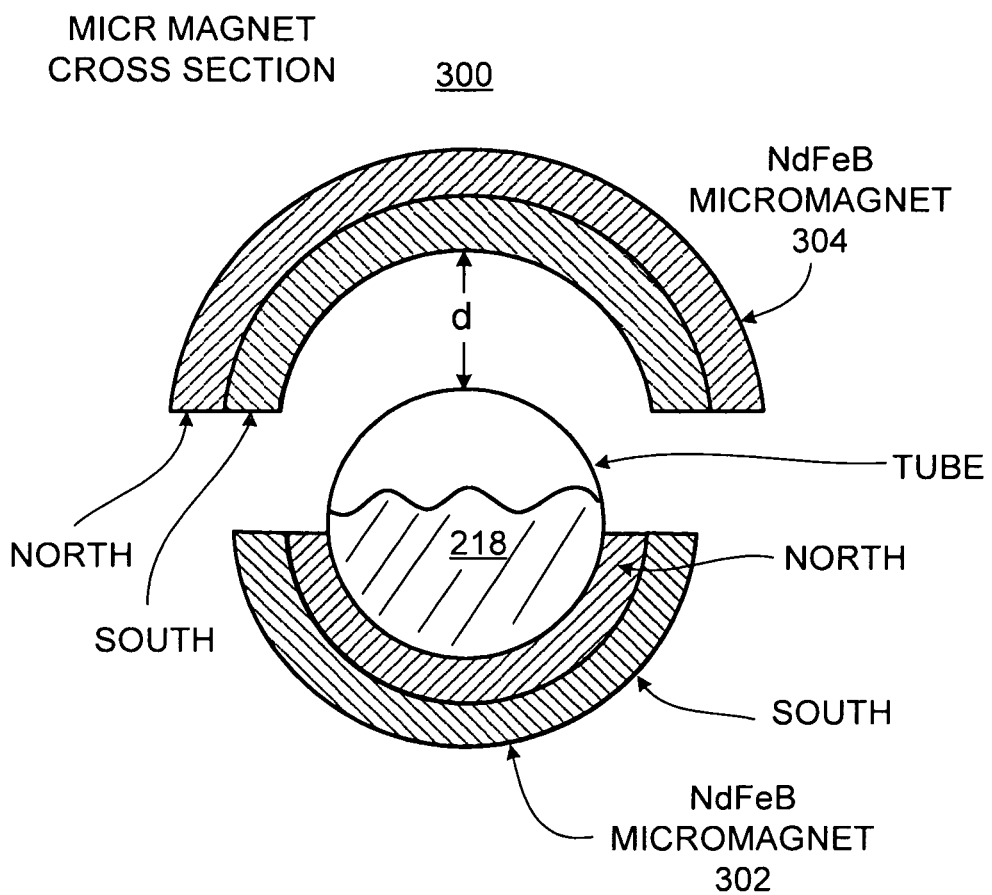
FIGS. 3A and 3B are schematic diagrams of a cross-sectional view and a side view, respectively, of an alternative implementation of a ferromagnetic fluid valve.
Figure 3B:
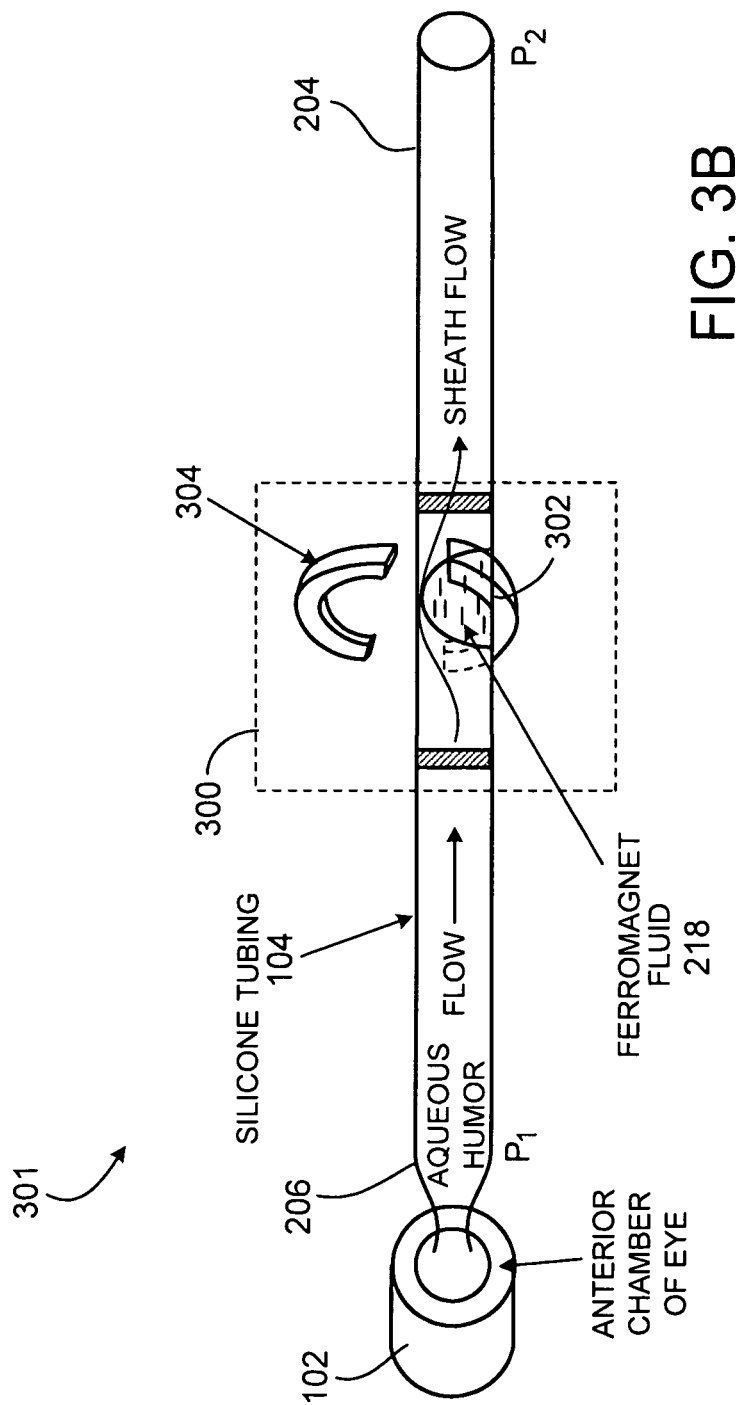
Figure 3C:
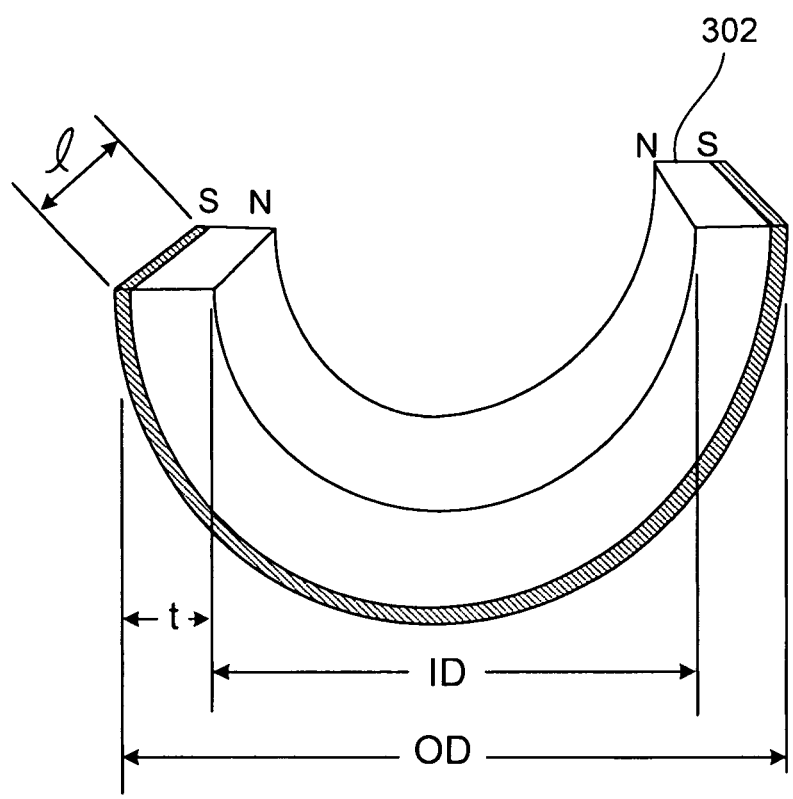
FIG. 3C is a schematic diagram of a magnet included in the ferromagnetic fluid valve of FIG. 3A.

FIGS. 3A and 3B illustrate a cross-sectional view and a side view, respectively, of an alternative implementation of a magnetic valve, here shown as valve 300 in a valve system 301. In this implementation, first and second semicircular magnets 302, 304 (FIG. 3B) are used to control the position of the ferrofluid 218 within the tube 104. The first magnet 302 is positioned close to or in contact with the tube 104; the second magnet 304 is positioned opposite the first magnet 302 and at a greater distance from the tube. The magnets can be permanent magnets, such as neodymium magnets formed of an alloy of neodymium, iron, and boron (e.g., $Nd_2Fe_{14}B$). The polarities of the magnets are inverted such that, for instance, the North pole of the first magnet 302 and the South pole of the second magnet 304 are the closest to the ferrofluid. In some cases (e.g., for experimental use), the first and second magnets 302, 304 are mounted on support plates 306, 308, respectively, such as magnetic steel plates. FIG. 3C shows the semicircular magnets 302, 304

In the example valve 300, the magnets 302, 304 are neodymium magnets formed an alloy of neodymium, iron, and boron ($Nd_2Fe_{14}B$). Both the thickness t and the length l of the magnets are about 200-300 μm. The inner diameter (ID) of the first magnet 302 may be less than about 600 μm (e.g., about 570 μm or about 420 μm). The inner diameter of the second magnet is greater than or equal to the inner diameter of the first magnet, and may be less than about 800 μm (e.g., about 420 μm, about 470 μm, about 520 μm, about 570 μm, about 590 μm, about 640 μm, about 690 μm, or about 740 μm). The outer diameter (OD) of each magnet is equal to its inner diameter plus twice the thickness of the magnet. The support plates, if used, have a thickness of about 30-40 μm.

Operation of the Ferromagnetic Fluid Valves

Figure 4A:
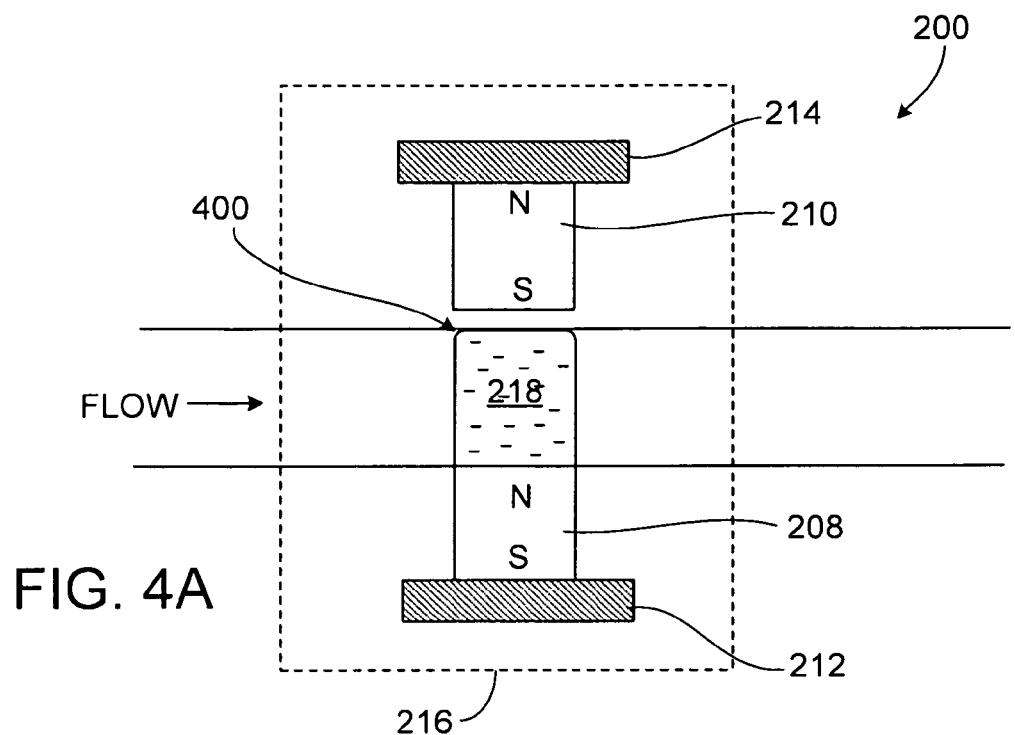
FIGS. 4A and 4B are schematic diagrams of the ferromagnetic fluid valve of FIG. 2 in an open and a closed configured, respectively.
Figure 4B:
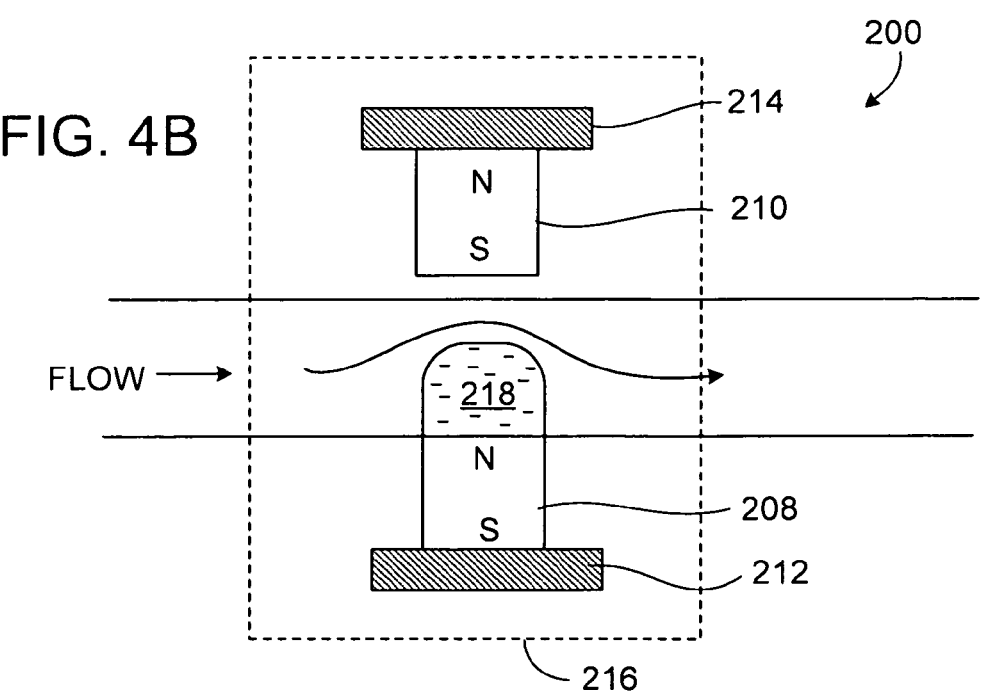
Figure 5A:
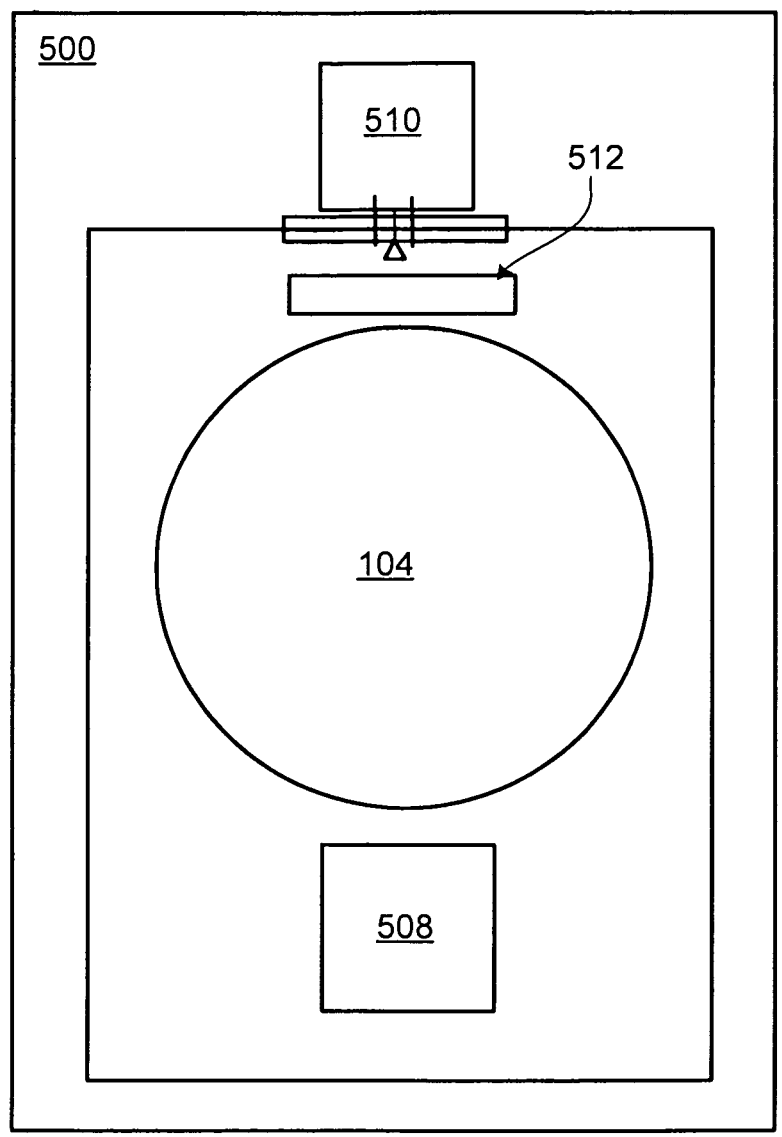
FIG. 5A is a cross-sectional schematic diagram of a variable magnetic membrane valve.
Figure 5B:
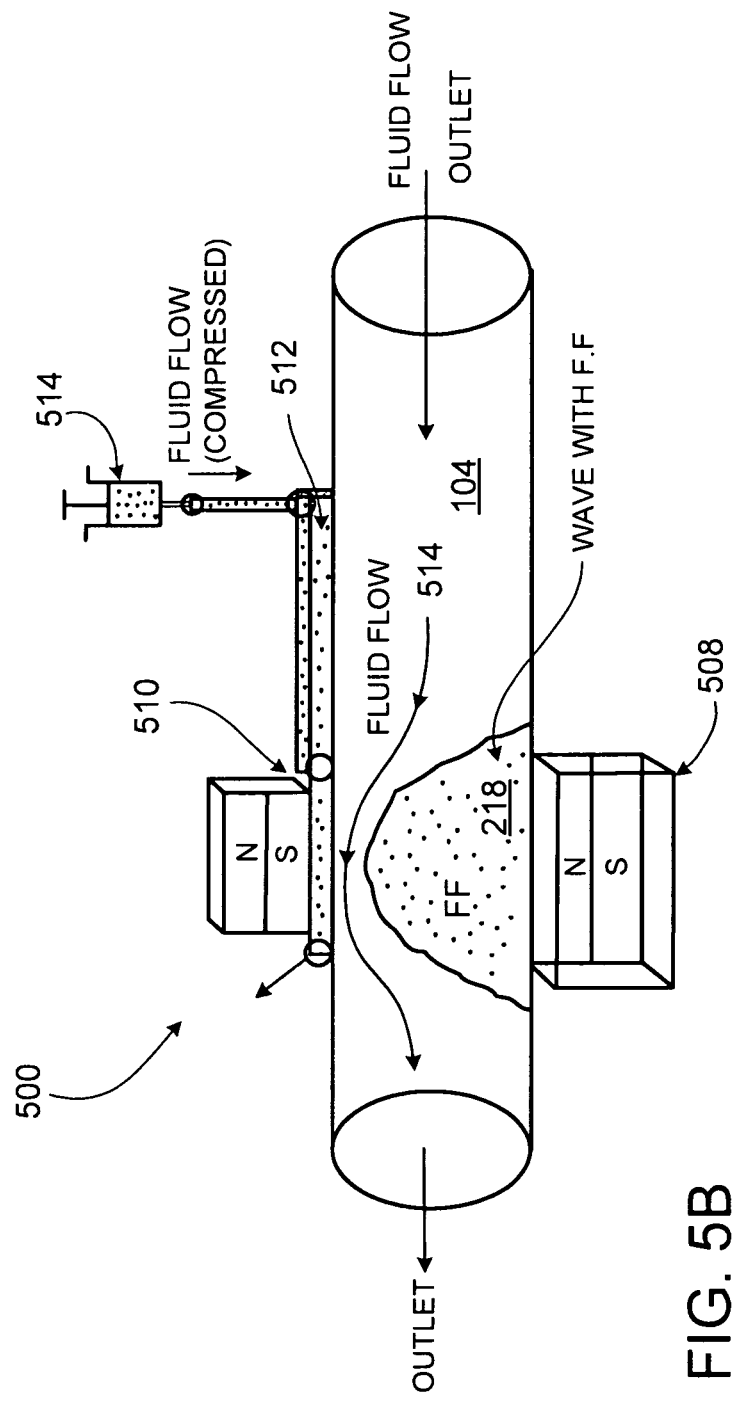
FIG. 5B is a side view schematic diagram of the variable magnetic membrane valve of FIG. 5A.
Figure 5C:
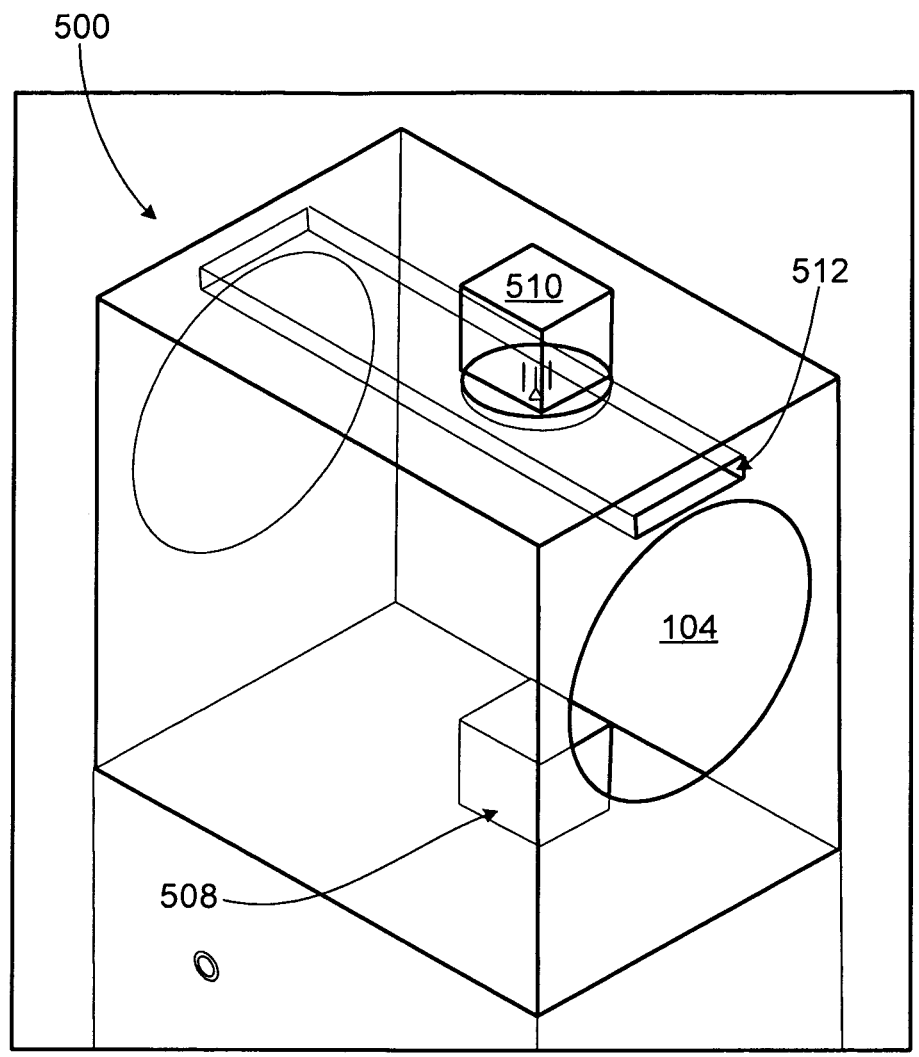
FIG. 5C is a perspective view schematic diagram of the variable magnetic membrane valve of FIG. 5A.
Figure 6:
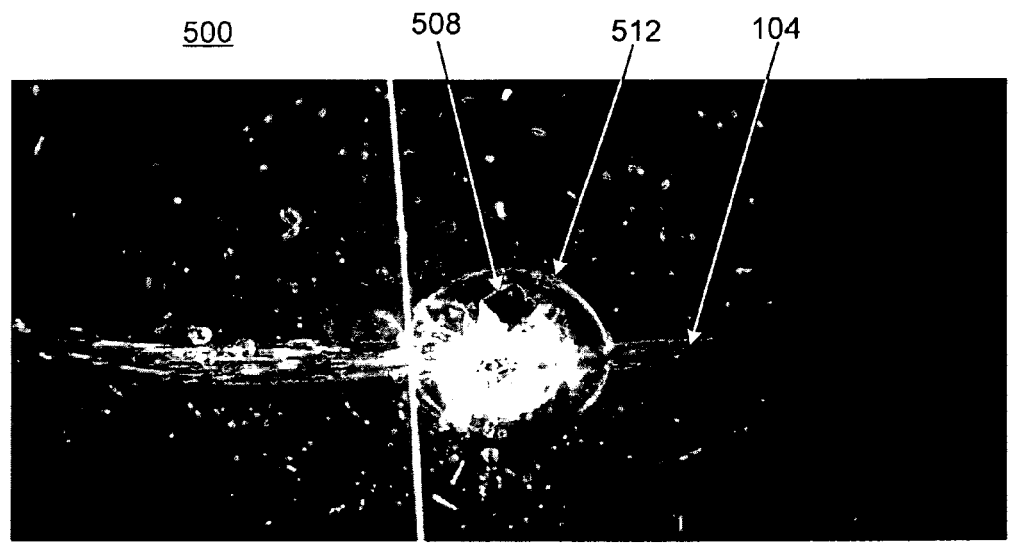
FIG. 6 is an optical microscope photograph of a prototype variable magnetic membrane valve.

FIGS. 4A and 4B illustrate the operation of an example of a magnetic valve 200. The first magnet 208 generates a magnetic field (the "fixation field") that attracts the ferrofluid 218, causing the ferrofluid 218 to contact the tube subsection 202 at the position of the first magnet 208 (e.g., around a location 400). The second magnet 210 also generates a magnetic field (the "second field") that attracts the ferrofluid 218. However, because the second magnet 210 is located farther away from the ferrofluid 218 than is the first magnet 208, the second field exerts a lower force on the ferrofluid 218.

In the absence of fluid in the tube 104, the second field is strong enough to attract the ferrofluid 218, causing the ferrofluid 218 to contact the tube subsection 202 at the position of the second magnet 208 (e.g., around a location 402). In this configuration, the ferrofluid 214 seals the tube and the valve is closed (FIG. 4A).

The valve 200 also remains closed for low fluid pressures in the tube 104. In particular, when the difference in fluid pressure between the distal end 206 and the proximal end 204 of the tube 104 is lower than a threshold opening pressure (i.e., when the pressure in the eye 102 is low to normal), the pressure exerted by the fluid in the tube on the ferrofluid 218 is not enough to overcome the magnetic attraction between the second magnet 210 and the ferrofluid. The ferrofluid 218 continues to seal the tube and the valve remains closed (FIG. 4A). In some cases, undesirable sheath flow may occur when the valve is closed (e.g., for gases or liquids with low surface tension). Sheath flow can be controlled (e.g., reduced or eliminated) by modification of the surface chemistry of the internal surface of the tube (e.g., by modifying the hydrophobic or hydrophilic nature of the surface).

As shown in FIG. 4B, the valve opens when the fluid pressure in the tube exceeds the threshold opening pressure. In particular, when the difference in pressure between the distal end 206 and the proximal end 204 of the tube 104 increases beyond the threshold opening pressure (i.e., when the pressure in the eye is high), the force generated by the pressure of the fluid in the tube on the ferrofluid 218 overcomes the magnetic attraction (force) between the second magnet 210 and the ferrofluid. The ferrofluid 218 moves out of contact with the tube around the location 402 and a channel 404 is opened through which fluid can flow in sheath flow for low pressures. However, the ferrofluid 218 is still held in position by the fixation field generated by the first magnet 208. With the magnetic field from the first magnet 208 and the laminar flow of the fluid in the tube acting on the ferrofluid, the ferrofluid collapses along the magnetic field lines of the fixation field, forming a bulk mass 306 on one side of the tube closest to the first magnet 208.

When the fluid pressure falls below a threshold closing pressure, the valve closes again (FIG. 4A). In particular, when the difference in pressure between the distal end 206 and the proximal end 204 of the tube 104 drops below the threshold closing pressure (i.e., when the pressure in the eye returns to a low level), the magnetic attraction between the second magnet 210 and the ferrofluid 218 overcomes the force generated by the fluid in the tube on the ferrofluid 218. The ferrofluid 218 again contacts the tube subsection 202 around location 402, sealing the tube and closing the valve.

The threshold opening and closing pressures are determined by the magnetic attraction between the second magnet 210 and the ferrofluid 218, among other parameters. The magnetic attraction, in turn, is dependent on the strength of the second magnetic field applied to the ferrofluid, which is a function of the strength and orientation of the second magnet, as well as the distance between the second magnet 210 and the tube subsection 202. Positioning the second magnet 210 closer to the tube subsection 202 produces a valve having higher threshold opening and closing pressures. Depending on the intended use for the valve, the second magnet can be placed at an appropriate distance to achieve the desired threshold pressures. In some examples, the distance between the second magnet 210 and the tube subsection 202 is adjustable, allowing the threshold pressures to be adjusted. The threshold opening and closing pressures are also determined by the volume and the magnetization of the ferrofluid and the cross sectional diameter of the tube.

In some examples, the internal portion of the tube subsection 202 is treated to control interactions between the ferrofluid and the tube and/or the flowing fluid and the tube. For instance, the region of the tube subsection around location 400 may be coated by a hydrophobic layer (e.g., via covalent bonding to the tube subsection using silanization techniques) to encourage a hydrophobic ferrofluid to stay in place or to allow the valve to open more easily. For instance, CYTOP™, an amorphous fluoropolymer with hydrophobic properties, can be covalently bonded to the tube subsection to create a hydrophobic surface within the tube. As another example, the region of the tube subsection around location 400 may be oxygen plasma treated or silanized with dipodal, polypodal or another network-forming silane to provide hydrophilicity, thus increasing the wettability of the surface and promoting sheath flow of fluid once the channel 204 is opened. In some cases, e.g., for liquids with high viscosity and/or high surface tension, the entire tube can be hydrophilic.

In some examples, the ferrofluid is a ferrowax in which the carrier fluid is a wax. When the temperature of the valve is below a threshold temperature (e.g., a flow temperature of the wax), the wax is solid and the valve is closed, regardless of the fluid pressure in the tube. When the temperature of the valve increases above the threshold temperature, the wax melts, activating the valve. The melted ferrowax is responsive to the fluid pressure in the tube as described above.

Referring to FIGS. 5A-5C and FIG. 6, in an alternative embodiment, a variable magnetic valve 500 opens or closes to allow or restrict fluid flow through the tube 104. A first magnet 508, such as an $Nd_2Fe_{14}B$ magnet, is positioned on a first side of the tube 104 and at a first, fixed distance from the tube (e.g., in contact with the tube). In some examples, the first magnet 508 is in contact with the tube. A second magnet 510 is positioned opposite the first magnet 508 with inverted polarity to the first magnet and at a greater distance from the tube than the first distance. A microfluidic channel 512 formed of a flexible membrane separates the second magnet 510 from the tube 104. When the channel 512 fills with fluid, the channel expands, forcing the separation between the second magnet 508 and the tube 104 to increase, weakening the magnetic interaction between the second magnet 508 and the ferrofluid 218 and reducing the threshold pressures of the valve. Conversely, when fluid is removed from the channel 512, the channel contracts, bringing the second magnet 508 closer to the tube 502, strengthening the magnetic interaction between the second magnet 508 and the ferrofluid 218 and increasing the threshold pressures of the valve. The amount of fluid in the channel 512 can be controlled by a pressure control device 514, such as a pump.

Figure 7:
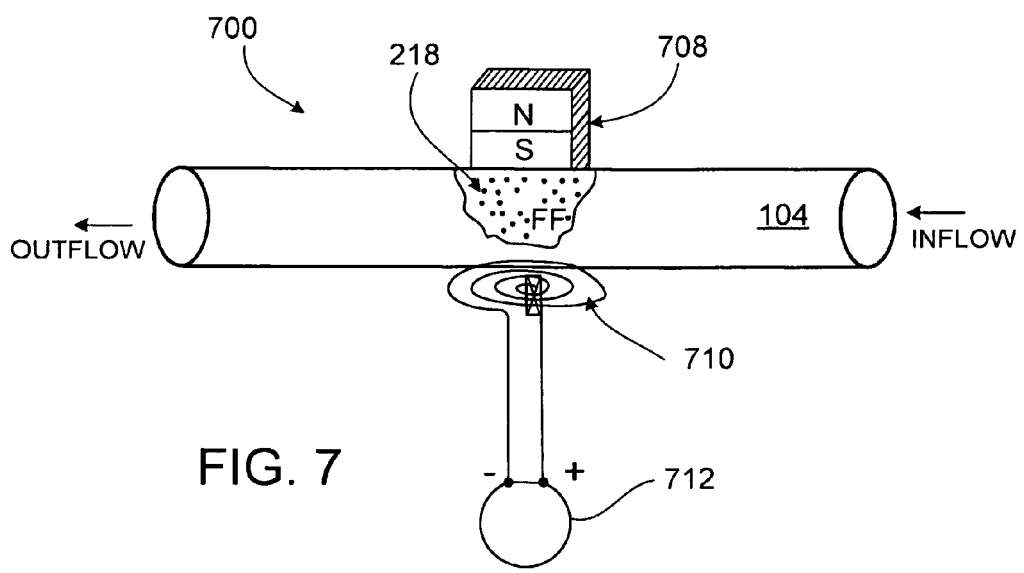
FIG. 7 is a schematic diagram of an alternative embodiment of a variable magnetic valve.

Referring to FIG. 7, in another alternative embodiment, a variable magnetic valve 700 opens or closes to allow or restrict fluid flow through the tube 104. A first magnet 708 is positioned on a first side of the tube 104 and at a first, fixed distance from the tube (e.g., in contact with the tube). An electromagnet 710 is positioned opposite the first magnet 708 as an independent element or as a complementary enhancer of a permanent magnet (not shown). The magnetic flux of the electromagnet 710 is changed using a voltage control 712, which changes the magnetic interaction between the electromagnet and the ferrofluid 218 and thus the threshold pressures of the valve. The electromagnet is, e.g., a spiral coil that directs the magnetic flux through its internal radius and towards the ferrofluid 218. In some examples, the electromagnet is printed using soft lithography techniques and includes an air core or a ferromagnetic core. In some examples, the electromagnet is complementary to a rare earth magnet, such as an NdFeB magnet.

Structure and Operation of a Ferromagnetic Membrane Valve

Figure 8A:
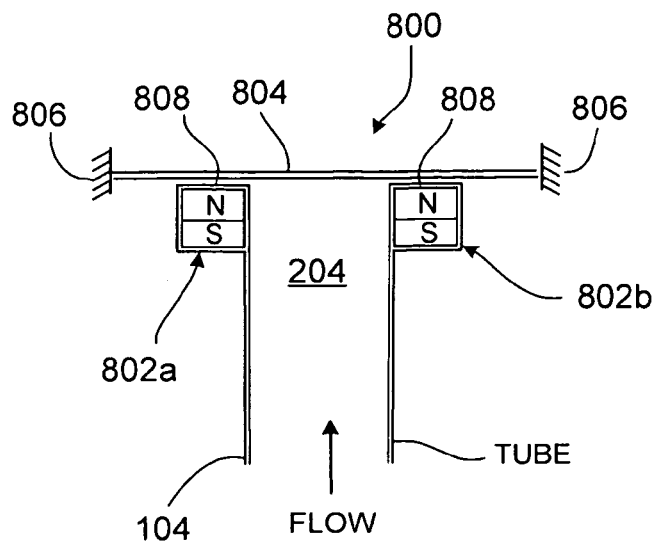
FIGS. 8A and 8B are schematic diagrams of a ferromagnetic membrane valve in an open and a closed configuration, respectively.
Figure 8B:
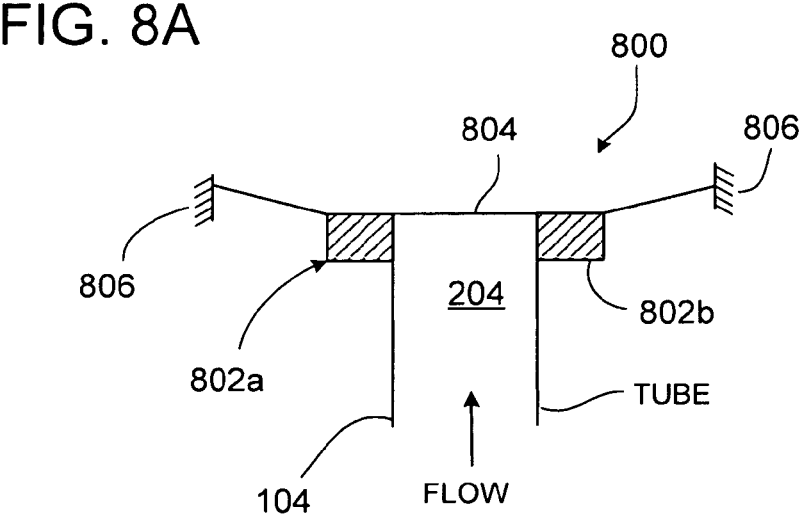

FIGS. 8A and 8B illustrate an example of a ferromagnetic membrane valve 800. The membrane valve 800 includes magnets 802a, 8026 (e.g., neodymium magnets) positioned at the proximal end 204 of the tube 104. A ferromagnetic membrane 804 is positioned across the proximal end 204 of the tube (i.e., perpendicular to the direction of flow through the tube) and attached to a support 806. In some implementations, the support 806 is a PDMS housing that at least partially surrounds (e.g., encircles) the proximal end of the tube. In some implementations, the ferromagnetic membrane 804 is covalently bonded to the support 806.

In some examples, the ferromagnetic membrane 804 is filled with a ferrofluid, such as the ferrofluid described herein. In other examples, the ferromagnetic membrane is doped with ferromagnetic particles (e.g., $Fe_3O_4$). For instance, a thin layer of ferromagnetic nanoparticles, such as ferrite nanoparticles, is coated (e.g., deposited or grown) onto one or both sides of the ferromagnetic membrane 804, or the ferromagnetic particles are incorporated in the membrane during formation using a non-polar surfactant. For instance, ferromagnetic particles can be mixed with PDMS liquid and cured to form a PDMS membrane having embedded magnetic particles. In some examples, the magnetic particles can be coated with a non-polar surfactant, which prevents agglomeration of the particles during mixing with the pre-polymer PDMS liquid. In some examples, the membrane surfaces can be treated with a hydrophobic coating, such as fluorosilane, to prevent the diffusion of water vapor into the membrane and the oxidization of the magnetic particles. Other materials can also be used to form the membrane. For instance, the membrane can be formed of rubbers, plastics, or other types of polymers with embedded magnetic particles. The magnets 802a, 802b generate magnetic fields that attract the ferromagnetic membrane 804. In the absence of fluid in the tube 104, the magnetic fields generated by the magnets 802a, 802b are strong enough to attract the ferromagnetic membrane 804. The ferromagnetic membrane 804 bends into contact with the magnets, sealing the end of the tube 104 and closing the valve (FIG. 8B).

The valve 800 remains closed for low fluid pressures in the tube. In particular, when the difference in fluid pressure between the distal end 206 and the proximal end 204 of the tube 104 is lower than a threshold opening pressure (i.e., when the pressure in the eye 102 is low), the pressure exerted by the fluid in the tube on the ferromagnetic membrane 804 is not enough to overcome the magnetic attraction between the magnets 802a. 802b and the membrane. The ferromagnetic membrane 804 continues to seal the tube and the valve remains closed.

As shown in FIG. 8A, when the fluid pressure in the tube exceeds the threshold opening pressure, the valve opens. In particular, when the difference in pressure between the distal end 206 and the proximal end 204 of the tube 104 increases beyond the threshold opening pressure (i.e., when the pressure in the eye is high), the pressure exerted by the fluid in the tube on the ferromagnetic membrane 804 overcomes the magnetic attraction between the magnets 802a, 802b and the membrane. The fluid pushes the ferromagnetic membrane 804 away from the magnets, opening channels 808 between the membrane and the magnets through which fluid can flow. For instance, when used in the eye, the valve can be designed to have a threshold opening pressure of 10 mm Hg, e.g., about 8, 9, 10, 11, or 12 mm Hg. The valve can be calibrated to operate at a desired opening pressure, e.g., a pressure equal to or less than about 33 mm Hg, by changing the thickness or composition of the membrane 804 or the structure of the valve 800.

When the fluid pressure falls back below the threshold closing pressure, the valve closes again (FIG. 8B). In particular, when the difference in pressure between the distal end 206 and the proximal end 204 of the tube 104 drops below the threshold closing pressure (i.e., when the pressure in the eye returns to a low level), the magnetic attraction between the magnets 802a, 802b and the ferromagnetic membrane 804 overcomes the pressure exerted by the fluid in the tube on the membrane. The ferromagnetic membrane 804 again contacts the magnets 802a, 802b, sealing the tube and closing the valve. For instance, when used in the eye, the valve can be designed to have a threshold closing pressure of 7 mm Hg, e.g., 5, 6, 7, 8, or 9 mm Hg. The valve can be calibrated to operate at a desired closing pressure, e.g., a pressure equal to or less than about 33 mm Hg, by changing the thickness or composition of the membrane 804 or the structure of the valve 800.

Figure 8C:
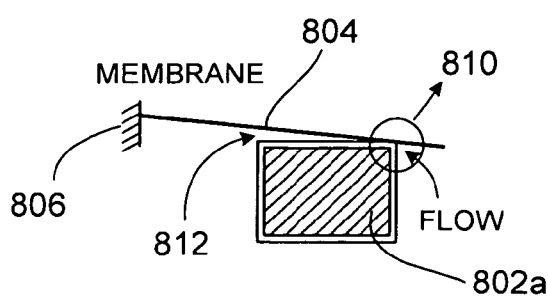
FIG. 8C is a schematic diagram of a section of the ferromagnetic membrane valve of FIGS. 8A and 8B.

In some examples, the surfaces of the magnets 802a, 802b are treated with hydrophobic and/or hydrophilic materials to assist in controlling fluid flow. For instance, as shown in FIG. 8C, an inside-facing surface and edge 810 of each magnet 802a, 802b is coated in a layer of hydrophobic material, such as CYTOP. When the valve 800 is closed and the ferromagnetic membrane 804 is in contact with the magnets 802a, 802b, the hydrophobic edge 810 prevents the fluid in the tube from wetting the surface of the tube, acting as a further flow barrier that prevents sheath flow between the ferromagnetic membrane and the magnets. A hydrophilic coating can also be used, e.g., on an outside-facing surface and edge 812 of each magnet 802a, 802b. The hydrophilic coating may be, e.g., a coating of a polar silanes such as polyhydroxylic groups, dipodal, polypodal or other network-forming silane. When the channels 806 are open, the hydrophilic edge 812 attracts the fluid in the tube, promoting sheath flow through the valve through surface wetting. In some implementations, the characteristics of these regions can be reversed such that the inside-facing surface 810 is hydrophilic and the outside-facing surface 812 is hydrophobic. In some examples, the surface of the PDMS membrane can also be treated with hydrophobic and/or hydrophilic materials.

In some examples, the thickness and composition (e.g., the quantity of ferromagnetic particles) of the membrane 804 can affect the threshold opening and closing pressures of the valve 800. The structure of the valve 800 can also affect its opening and closing pressures. For instance, the strength and area of the magnets 802a, 802b; the distance between the magnets 802a, 802b and the membrane 804; and the hydrophilic or hydrophobic surface properties of the membrane 804 and magnets 802a, 804b can all be designed and configured to affect the opening and closing pressures of the valve 800.

In some examples, a single circular magnet (e.g., a ring-shaped magnet) is used in place of the magnets 802a, 802b. In other examples, more than two magnets are used. For instance, four magnets can be distributed evenly around the circumference of the tube 104.

Figure 9A:
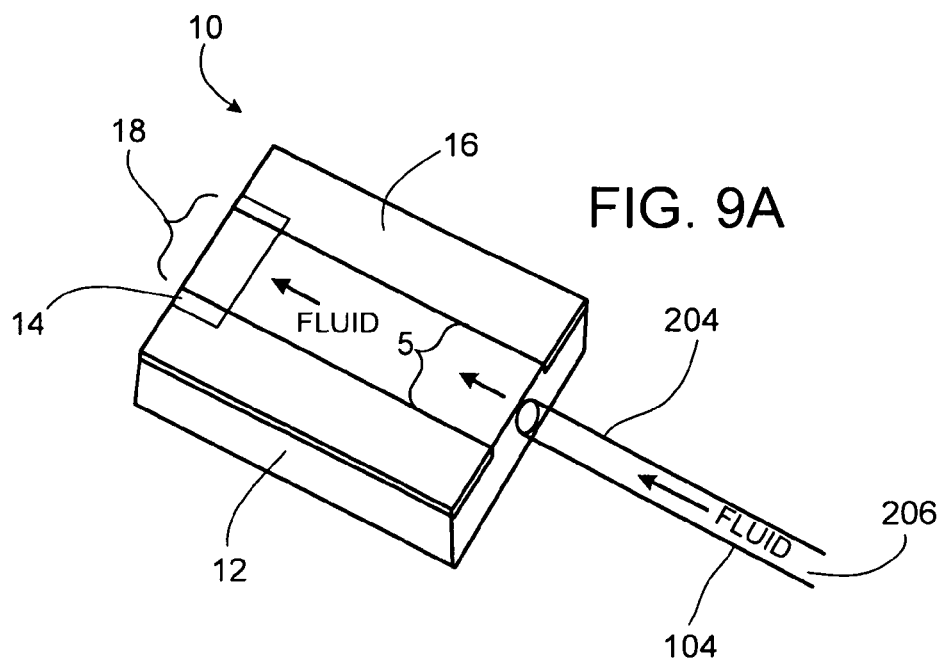
FIG. 9A is a perspective view schematic diagram of an alternative embodiment of a ferromagnetic membrane valve.
Figure 9B:
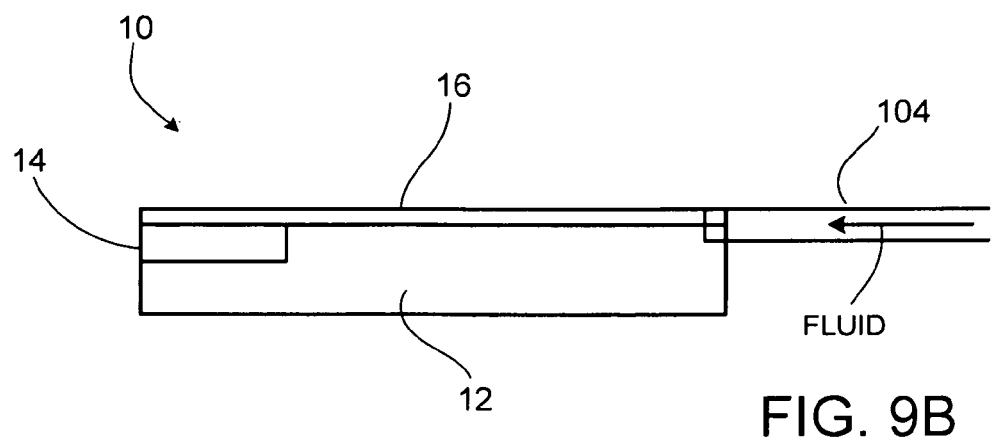
FIG. 9B is a side view schematic diagram of the ferromagnetic membrane valve of FIG. 9A in a closed configuration.
Figure 9C:
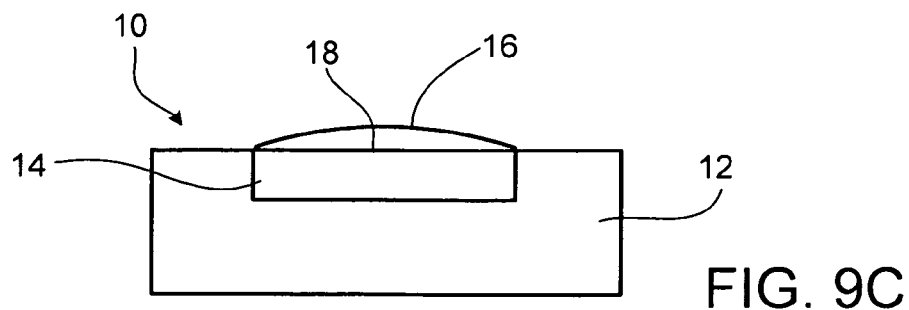
FIG. 9C is a front view schematic diagram of the ferromagnetic membrane valve of FIG. 9A in an open configuration.

FIGS. 9A-9C illustrate another example of a magnetic membrane valve 10. In this example, the membrane valve 10 includes a valve housing 12 attached to the proximal end 204 of the tube 104. For instance, the housing 12 can be formed of PDMS. One or more magnets 14 (e.g., neodymium magnets) are embedded into the housing 12 and exerts a magnetic force on a magnetic membrane 16, which is positioned flat on the top of the housing 12 (i.e., parallel to the direction of flow through the tube). The encapsulation of the magnet 14 in the PDMS housing 12 can help to avoid fluid coming into contact with the magnet 12, thus providing good biocompatibility and corrosion resistance. The membrane 16 is formed of a polymer, such as PDMS, with magnetic particles (e.g., $Fe_3O_4$ particles) embedded therein. The membrane 16 is bonded to the housing 12 on two sides, leaving an unbounded flow path 18 in the center of the membrane 16.

The magnet 14 generates a magnetic field that attracts the membrane 16. In the absence of fluid in the tube 104, the magnetic field generated by the magnet 14 is strong enough to attract the membrane 16, causing the membrane 16 to remain in flush contact with the housing 12 in the region of the magnet 14 (FIG. 9B). This configuration seals the end of channel 18, closing the valve 10.

The valve 10 remains closed for low fluid pressures in the tube. In particular, when the difference in fluid pressure between the distal end 206 and the proximal end 204 of the tube 104 is lower than a threshold opening pressure of the valve 10 (i.e., when the pressure in the eye 102 is low), the pressure exerted by the fluid in the tube on the membrane 16 is not enough to overcome the magnetic attraction between the magnet 14 and the membrane 16. The membrane 16 continues to seal the channel 18 and the valve 10 remains closed (FIG. 9B).

As shown in FIG. 9C, when the fluid pressure in the tube exceeds the threshold opening pressure of the valve 10, the valve opens. In particular, when the difference in pressure between the distal end 206 and the proximal end 204 of the tube 104 increases beyond the threshold opening pressure of the valve 10 (i.e., when the pressure in the eye is high), the pressure exerted by the fluid in the tube on the membrane 16 overcomes the magnetic attraction between the magnet 14 and the membrane 16. The fluid causes the membrane 16 to deflect away from the magnet 14, opening the channel 18 and allowing fluid to flow through the valve 10. For instance, when used in the eye, the valve can be designed to have a threshold opening pressure of 10 mm Hg, e.g., about 8, 9, 10, 11, or 12 mm Hg. The valve can be calibrated to operate at a desired opening pressure, e.g., a pressure equal to or less than about 33 mm Hg, by changing the thickness or composition of the membrane 16 or the structure of the valve 10.

When the fluid pressure in the tube falls back below the threshold closing pressure, the valve 10 closes again (FIG. 9B). In particular, when the difference in fluid pressure between the distal end 206 and the proximal end 204 of the tube 104 drops below a threshold closing pressure of the valve 10 (i.e., when the pressure in the eye 102 returns to a low level), the magnetic attraction between the magnet 14 and the membrane 16 overcomes the pressure exerted by the fluid in the tube on the membrane 16. The membrane 16 contacts the housing 12 in the region of the magnet 14, sealing the channel 18 and closing the valve 10. For instance, when used in the eye, the valve can be designed to have a threshold closing pressure of 7 mm Hg, e.g., 5, 6, 7, 8, or 9 mm Hg. The valve can be calibrated to operate at a desired closing pressure, e.g., a pressure equal to or less than about 33 mm Hg, by changing the thickness or composition of the membrane 16 or the structure of the valve 10.

In some examples, the membrane 16 can be formed by curing a mixture of PDMS liquid and ferromagnetic particles. The thickness of the membrane can be, e.g., between about 200-350 µm. Both the thickness of the membrane and its composition (e.g., the ratio between PDMS and $Fe_3O_4$ embedded in the PDMS) can affect the opening and closing pressures of the valve 10. The structure of the valve 10 can also affect its opening and closing pressures. For instance, the strength and area of the magnet 14; the hydrophilic or hydrophobic surface properties of the membrane 16, housing 12, and magnet 14; and the presence of structures in the channel 18 can all be designed and configured to affect the opening and closing pressures of the valve 10.

To form the channel 18, the membrane 16 and the housing 12 are treated with a plasma oxygen treatment to covalently bond the membrane 16 to the housing 12. The area of the channel 18 on both the membrane 16 and the housing 12 are masked, e.g., by covering the areas with a thin plastic film, to avoid exposing the channel area to the oxygen plasma. Bonding between the membrane 16 and the housing 12 does not occur in the masked areas, thus forming the channel 18. That is, as a result of the plasma treatment, the membrane 16 and the housing 12 are bonded together except in the unexposed region, where the membrane 16 and the housing 12 are not bonded. In other types of polymers and plastics, heat molding or glue can be used for membrane bonding.

EXAMPLES

The invention is further described in the following examples, which do not limit the scope of the invention described in the claims. The following examples generally show the fabrication and operation of a magnetic valve and demonstrate the effect of fluid flow on the configuration of the valve. The examples also describe the experimental use of a magnetic valve in vivo in rabbits.

Example 1—Examples of Operational Parameters of a Magnetic Valve

In this example, valve 200 shown in FIG. 2 has an inner diameter of tube 104 of about 300 µm. The tube has a flow capacity of about 2-3 µL/minute and supports a flow speed of about 35 mm/minute at a flow capacity of 2.5 µL/minute. These parameters are generally sufficient to provide adequate drainage of aqueous humor from the eye.

The magnets 208, 210 are $\frac{1}{16}$" square neodymium magnets formed an alloy of neodymium, iron, and boron ($Nd_2Fe_{14}B$, K&J Magnetics, Inc., Jamison, Pa.). The surface field of each magnet is 5754 Gauss providing a pulling force of 0.14 Lbs. The maximum energy product ((BH)max) of each magnet is about 42 MGauss.Oersted. The first magnet 208 is in contact with the tube subsection 202 and the second magnet 210 is positioned about 100 µm from the tube subsection 202.

A fraction of a microliter (about 0.1 µL) of ferrofluid 218 is positioned in the tube subsection 202 between the first magnet 208 and the second magnet 210. The ferrofluid includes 10 nm diameter ferrite (e.g., $Fe_3O_4$ or $BaFe_{12}O_{19}$) nanoparticles coated with a surfactant and suspended in a hydrocarbon or fluorocarbon carrier fluid.

The valve 200 in this example operates with an opening threshold pressure of 10 mm Hg and a closing threshold pressure of 7 mm Hg. Thus, when the pressure in the tube 104 increases beyond 10 mm Hg, the valve opens, and when the pressure drops below 7 mm Hg, the valve closes.

Example 2—Fluid Flow Through the Magnetic Valve

Figure 10:
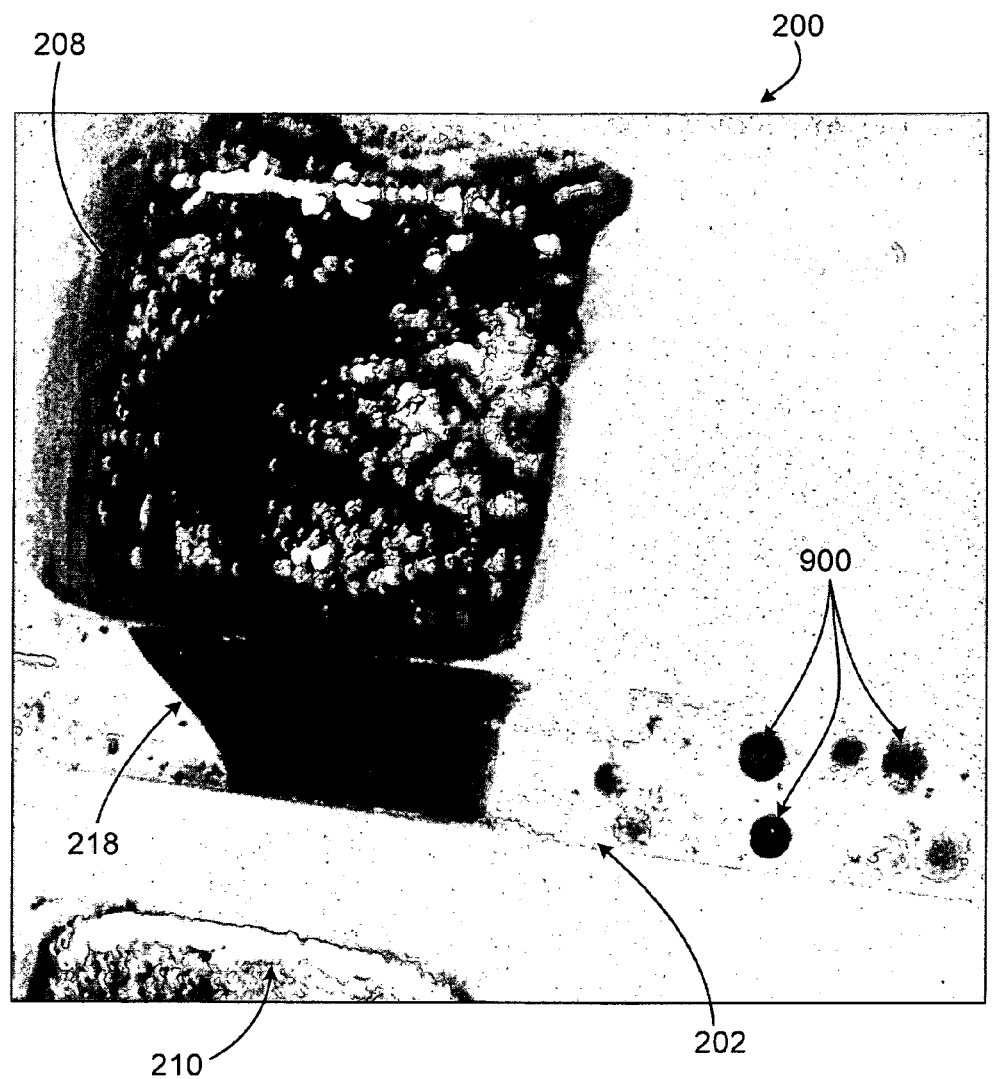
FIG. 10 is an optical microscope photograph of an example of a ferromagnetic fluid valve.

Referring to FIG. 10, in this example, magnetic valve 200 has the geometry described in Example 1 and is used to control the flow of distilled water ($dH_2O$) through the tube 104. The inner and outer diameters of the fused silica tube were 300 µm and 400 µm, respectively. The length of the tube subsection 202 was 300 mm and the length of the connector silicone tube 104 was 40 cm. In this example, the ferrofluid 218 includes 10 nm diameter ferrite particles dispersed in a liquid hydrocarbon carrier fluid (NF-3905, Ferrotec, Bedford, N.H.).

After four days of continuous flow of $dH_2O$ at 2.5 µL/minute, pieces 900 of the ferrofluid 218 had broken off and started to flow downstream, indicating that a ferrofluid valve formed of a hydrocarbon-based ferrofluid may not withstand long-term flow.

In contrast, a ferrofluid valve formed of a fluorocarbon-based ferrofluid in a tube of the same dimensions is more stable and does not denature or break apart with long-term flow. In a continuous flow at a pressure of 15 mm Hg, the mean flow was calculated at 3.5 µl/min over a period of 45 days. Small flow variations were noted between days. At a continuous pressure of 7 mm Hg, no flow was observed over a period of 7 days. Over a period of 30 days in which the pressure was altered between 7, 12, 16, and 21 mm Hg, the opening and closing pressure was maintained within ±1 mm Hg throughout the 30 day period while flow was increased for higher pressures (1.8 µl/min at 12 mm Hg; 14.3 µl/min at 16 mm Hg; 7.6 µl/min at 21 mm Hg).

In another example, a magnetic valve including a tube having inner and outer diameters of 400 µm and 550 µm, respectively, was used to control the flow of dH$_2$O through the tube. The length of the tube subsection 202 was 300 mm and the length of the silicone tube 102 was 40 cm. Similar results were observed.

Example 3—Flow Capacity of the Magnetic Valves

The pressure/flow characteristics of the magnetic valve were evaluated over time under different pressure regimes. The intraocular pressure (IOP) is a function of the outflow capacity of the eye versus the aqueous humor production rate at a given pressure. Thus, at a given IOP, the flow capacity of the valve should be able to handle the volume of aqueous humor that is produced in the eye per unit time.

Figure 11:
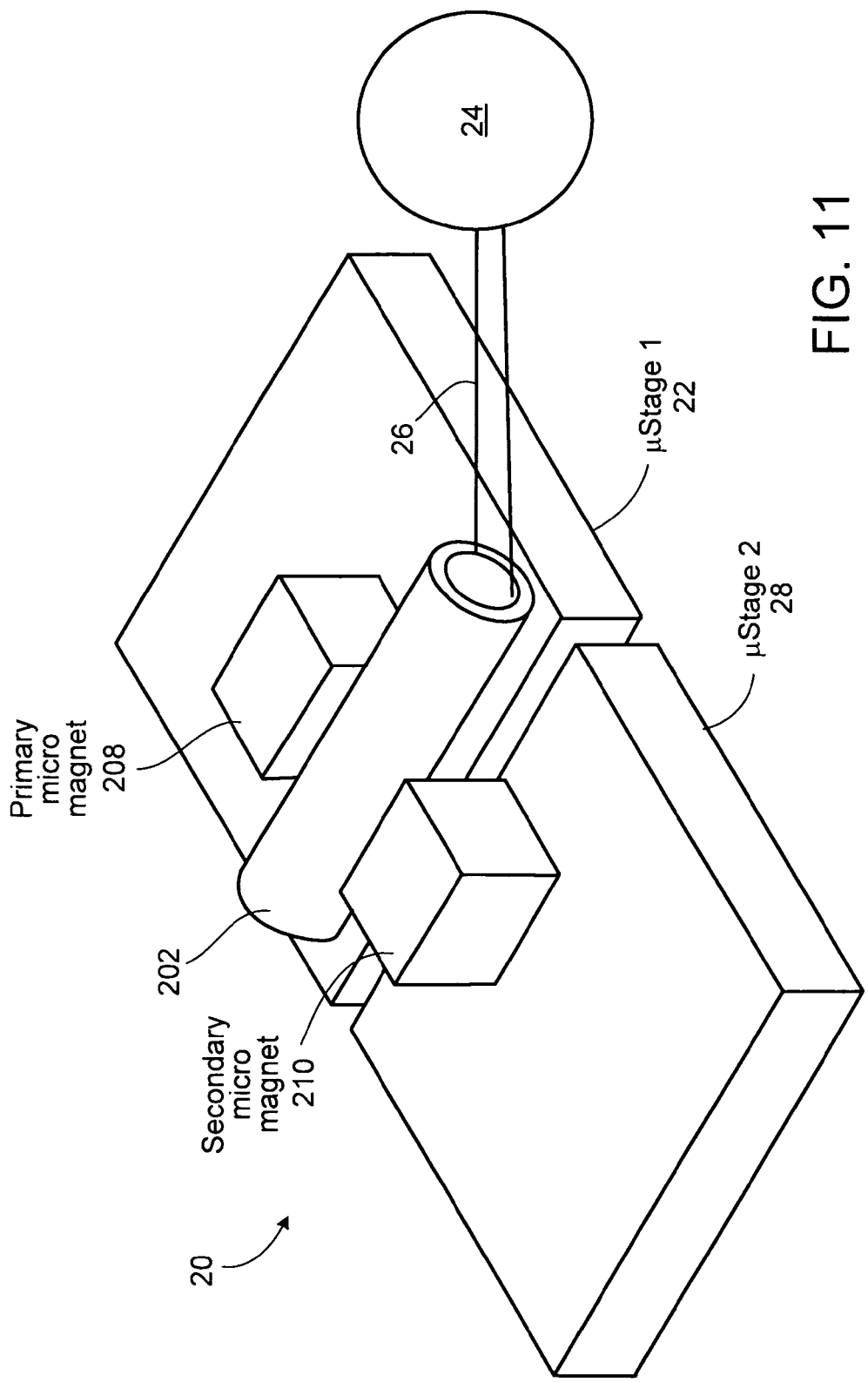
FIG. 11 is a diagram of a modular test system used to test the pressure/flow characteristics of a ferromagnetic fluid valve.

Referring to FIG. 11, the pressure/flow characteristics were tested using a modular test system 20 in which the magnets 208, 210 were able to be moved relative to the tube subsection 202 containing the ferrofluid. The tube subsection 202 was placed on a microstage 22 (Thorlabs, Newton, N.J.) and connected to a reservoir 24 containing distilled water (dH$_2$O) via a 40 cm silicone tube 26 (VWR International 60985-700, 0.30 mm inner diameter, 0.61 mm outer diameter). The first magnet 208 was placed adjacent to the tube subsection 202 with its north magnetic pole facing toward the tube subsection 202. The second magnet 210 was placed on a separate microstage 28 with its south magnetic pole facing the first magnet 208 and offset horizontally along the flow direction relative to the first magnet 208. That is, the modular test system 20 replicated the configuration of the magnetic valve 200 while providing the ability to adjust the distance between the second magnet 210 and the ferrofluid within the tube subsection 202. Each magnet had a surface field of 5754 Gauss providing a pulling force of 68 g. The maximum energy product ((BH)max) of each magnet was about 42 MGauss.Oersted.

The dH$_2$O reservoir 24 was elevated to a defined height to generate a hydrostatic pressure, as calculated using the following formula:

$$P=\rho gh,$$

where P is the pressure, $\rho$ is the density of the liquid, g=9.8 N/kg of gravitational acceleration, and h is the height of the reservoir in meters. The hydrostatic pressure was converted to millimeters of mercury pressure from the reservoir. The flow rate through the valve was measured as a function of pressure. Measurements were carried out continuously for three months. Various test pressures were set by adjusting the height of the reservoir.

Experimental results at a reservoir pressure of 7 mm Hg over a period of one week showed no flow or significant leakage.

Figure 12:
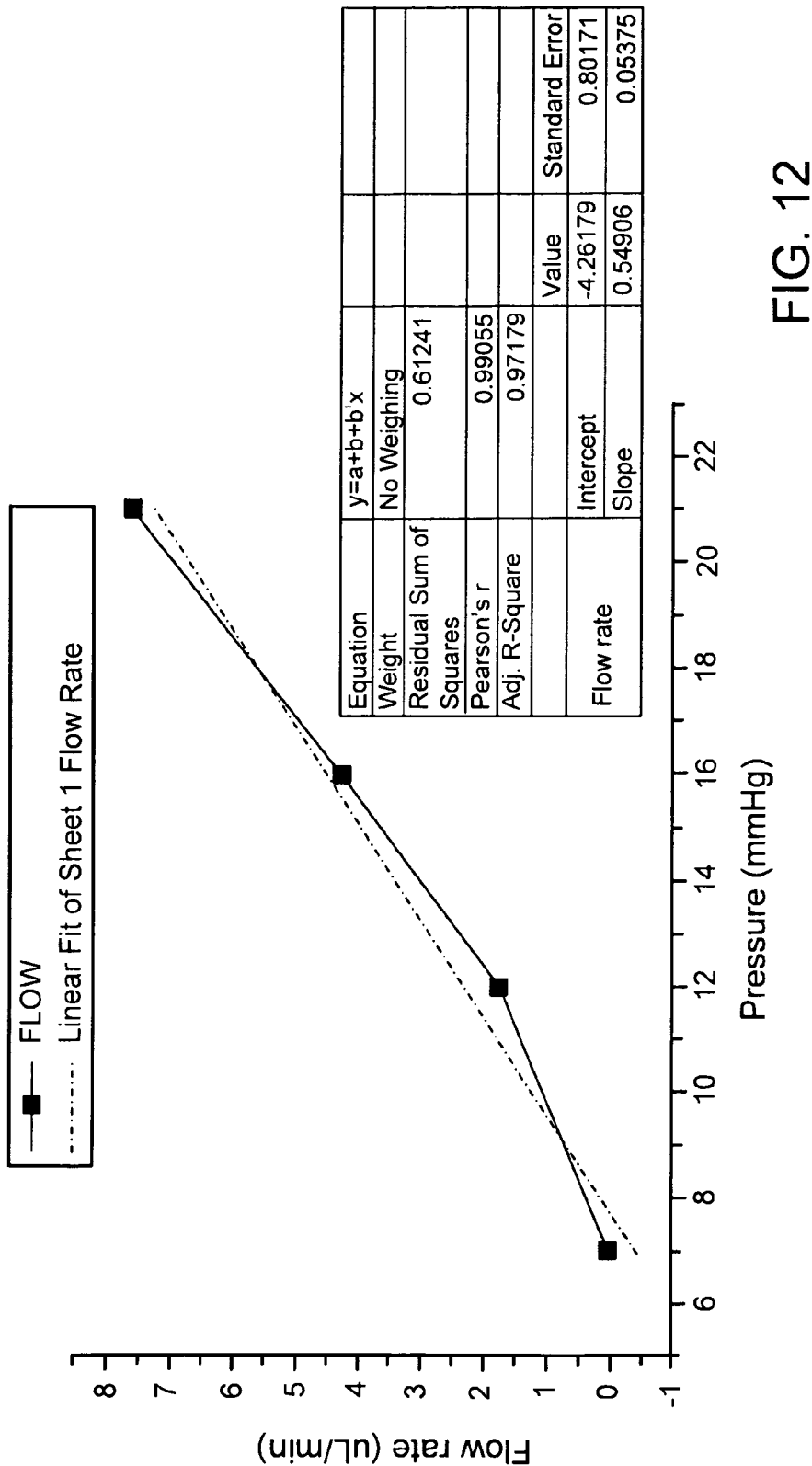
FIG. 12 is a plot of flow rate versus pressure for a ferromagnetic fluid valve.

Over a period of thirty days, the reservoir pressure was varied among 7, 12, 16, and 21 mm Hg. The resulting opening and closing pressures of the valve were maintained at 10 mm Hg and 7 mm Hg, respectively, by adjusting the distance between the second magnet 210 and the tube subsection 202. Small variations of less than ±0.5 mm Hg were permitted. The flow/pressure response of the valve showed an increased flow at higher reservoir pressures: 1.8 µl/min at 12 mm Hg, 4.3 µl/min at 16 mm Hg, and 7.6 µl/min at 21 mm Hg. Flow variations were clinically insignificant during the study period (±0.2 µL/min at 12 mm Hg). Referring to FIG. 12, a linear response was found between flow and pressure (adjusted $R^2$=0.971). The results in FIG. 12 represent the mean flow rate at 7, 12, 16, and 21 mm Hg of reservoir pressure over a period of three months.

At 12.5 mm Hg of pressure, the outflow facility achieved by the valve was approximately equal to the aqueous humor production rate in normal human eyes (~2.5 µL/min). These results suggest that the pressure in the eye cannot exceed an upper threshold of 12.5 mm Hg without overwhelming the flow capacity of the valve, even if the valve filters the total aqueous humor volume produced per minute. However, some functionality may remain at the principal draining sites in the normal eye, such as the trabecular meshwork and the uveo-scleral pathway in the eye, and thus some of the produced aqueous humor can be drained through these draining sites. In this case, the opening pressure to be handled by the valve can be reduced from 12.5 mm Hg to about 10 mm Hg. Based on the linear relationship between flow rate and pressure (FIG. 12), this reduction in opening pressure indicates that the valve can drain approximately 50% of the aqueous humor produced per minute.

Example 4—Use of the Magnetic Valves in Rabbits

In vivo experiments were conducted to test the ability of magnetic valve systems to drain fluid from the eye of a rabbit. All animal procedures were performed in accordance with the ARVO Statement for the use of Animals in Ophthalmic and Vision Research and the National Institute of Health Guidance for the Care and Use of Laboratory Animals.

Magnetic valves were implanted in three NZ White/NZ Red crossed rabbits (male, weighing 4.3-4.5 kg). The valve was connected with 35 mm of silicone tubing (inner diameter 300 µm, outer diameter 610 µm) that was trimmed during the surgery and placed at the lower lid fornix temporally. The tubing was then inserted beneath the conjunctiva and was led up to the supra-temporal limbus. The tip was inserted into the posterior chamber of the eye using a 25 G needle. A small circular peg, previously attached to the tubing, was anchored to the sclera with two 10-0 Nylon sutures for stability. Thus, the tubing extended subconjunctivally to enter the eye from a point in the lower fornix. The ferrovalve housing remained exterior to the conjunctiva at the inferior lid fornix. The mean time of surgery was about 40 minutes.

Figure 13:
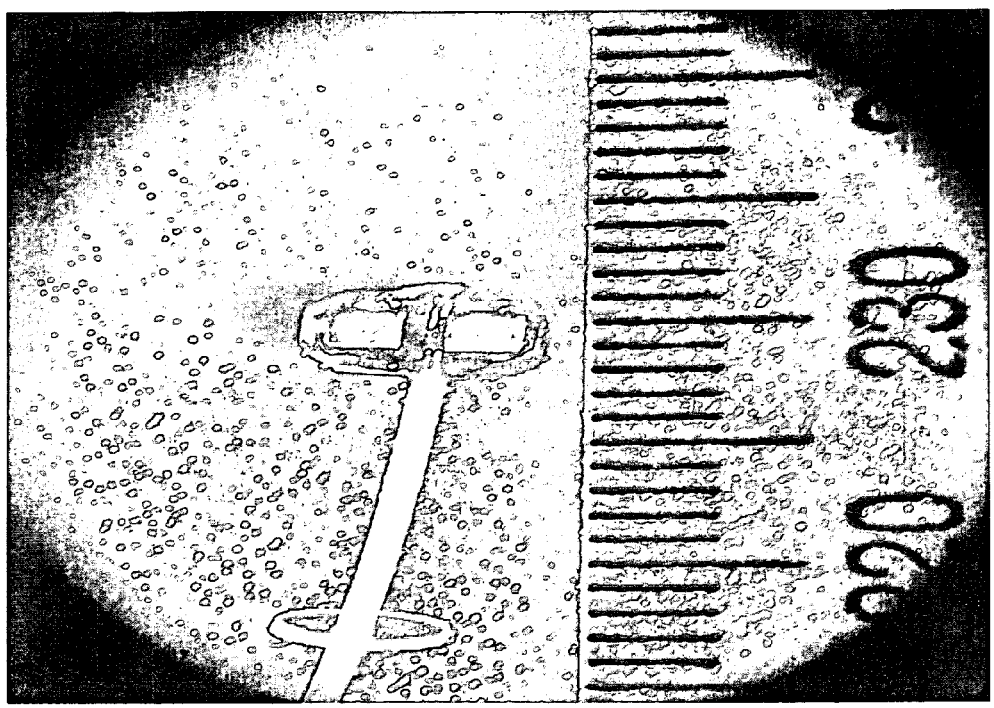
FIG. 13 is an optical microscope photograph of a prototype implantable ferromagnetic fluid valve.

An example of an implantable valve 950 used in the rabbits is shown in FIG. 13. The valve 950 is less than 1 cm in length and 0.5 cm in width and includes two NdFeB magnets each having a volume of 1 mm$^3$. The valve also includes a fused silica tube subsection that is 400 µm in diameter and 2.5 mm in length connected to a longer silicone tube.

The animals were treated daily with topical Polytrim™ (polymyxin B/trimethoprim, Allergan, Inc., USA) and Pred-Forte™ (prednisolone acetate 1%, Allergan, Inc., USA), and followed for two weeks. Eyes were assessed for inflammation and infection and daily IOP measurements were performed. During the two weeks of follow-up, no signs of infection or inflammation were observed other than a brief period of irritation immediately following the surgery. The circular PDMS peg used around the tube provided good fixation to the sclera with additional sealing of the scleral tunnel.

Mean IOP values in the valve-implanted eye (11.8±2 mm Hg) were significantly lower than mean IOP values in the contralateral control eye (14±3 mm Hg) (P<0.0001, paired sample t-test). These values are in agreement (±2 mm Hg) with those obtained in vitro.

At the last follow-up, two weeks after surgery, a continuous flow was still observed at the outlet tip of the valve, demonstrated continued functionality of the magnetic valve.

Example 5—Fabrication of the Magnetic Valves

In one example, magnetic valves were fabricated using molding and soft lithography techniques. A master mold was created using permanent epoxy negative photoresist (SU-8 3050, MicroChem®, Newton, Mass.). The photoresist was spin coated (1000 rpm) onto a 3-inch silicon wafer and exposed to ultraviolet light through a photo mask with 100 μm features. After developing the master, PDMS was poured over the master and cured by baking at 65° C. overnight to form a master mold.

A capillary tube of clear fused quartz (VitroCom, Mountain Lakes, N.J.) with inner diameter (ID) 300 μm and outer diameter 400 μm was silanized by flushing the tube with a polyethylene glycol (PEG)-silane solution ([methoxy(polyethyleneoxy)propyl]trichlorosilane, SIM6492.66, Gelest®, Inc., Morrisville, Pa.). The capillary was cut to a length of 5.5 mm using a diamond blade and inserted into a soft silicone tube of 300 μm ID and 610 μm OD (VWR International 60985-700). The tube was mounted on the cured PDMS mold with two 1/16-inch cubic rare earth magnets ($Nd_2Fe_{14}B$, K&J Magnetics, Inc., Jamison, Pa.). The PDMS mold was placed on a silicon wafer in a petri dish and a PDMS pre-polymer (Sylgard 184 (Dow Corning® Corporation, Midland, Mich.) flexible silicon elastomer with a base to curing agent ratio of 10:1 by weight) was poured and cured at 65° C. overnight to embed the capillary tube and magnets in PDMS.

After curing, the device was cut out from the bulk PDMS and trimmed to a size of 2.8×4.7×2.7 mm (length×width×height). One millimeter length of silicone tube was left on both sizes of the cut device for tube connection. A stainless steel tube of 400 μM OD and 12 mm length (New England Small Tube, Litchfield, N.H.) was used to interconnect the silicone tube with a longer soft silicone tube (VWR International 60985-700). The tube connections were secured with PDMS.

A small amount of ferrofluid (~0.1 μL)(Ferrotec) was introduced into the capillary using a 30-gauge needle. The ferrofluid was made of 10 nm monodisperse $Fe_3O_4$ particles suspended in a fluorocarbon carrier oil. The ferrofluid had a viscosity of 367 cP and a maximum magnetization of 404 Gauss (NF 3914). The ferrofluid was securely fixed by the magnetic force of the two rare earth magnets.

Example 6—Characterization of the Ferrofluid

Figure 14A:
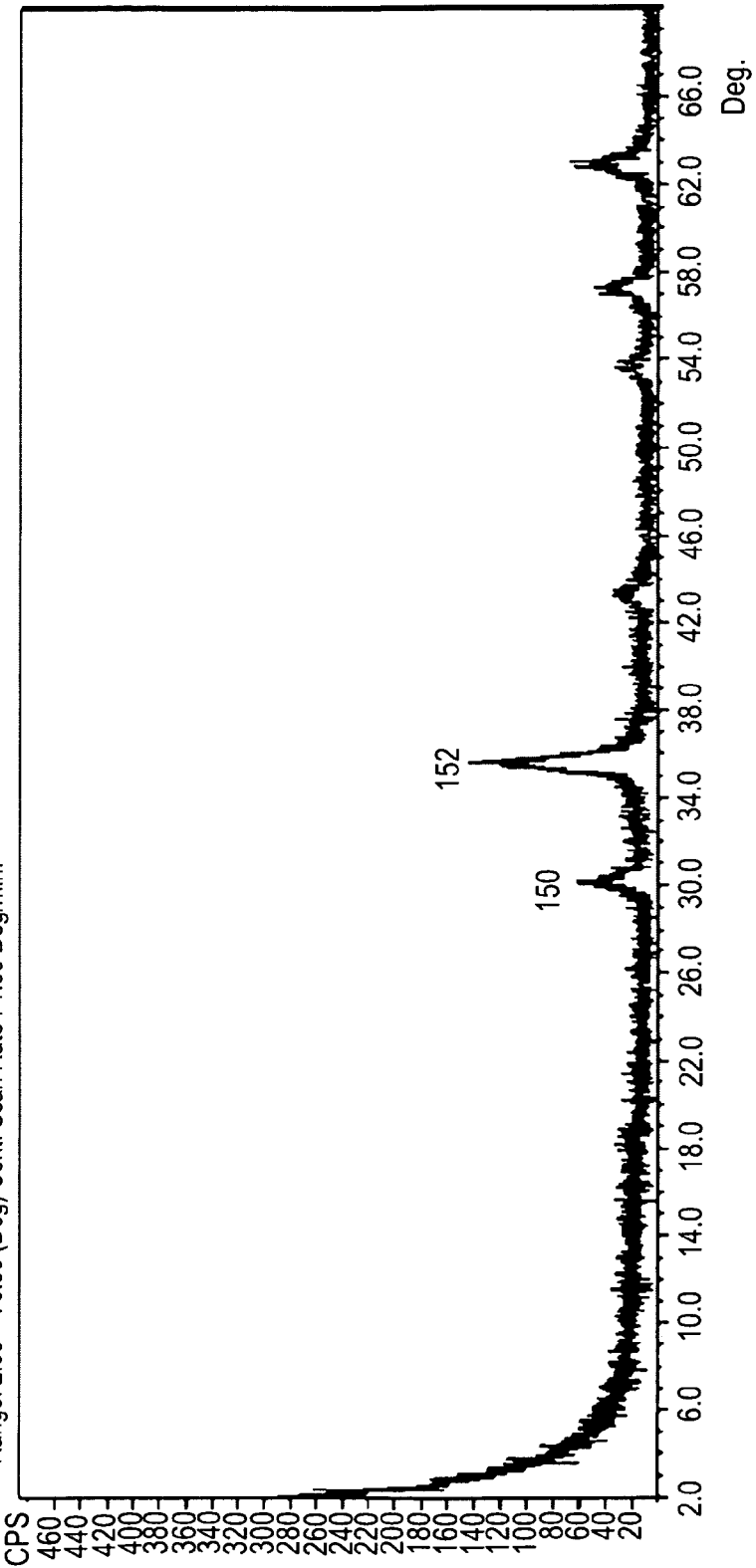
FIGS. 14A and 14B are X-ray diffraction plots of a ferrofluid after exposure to oxygen and water for 24 hours and 8 weeks, respectively.
Figure 14B:
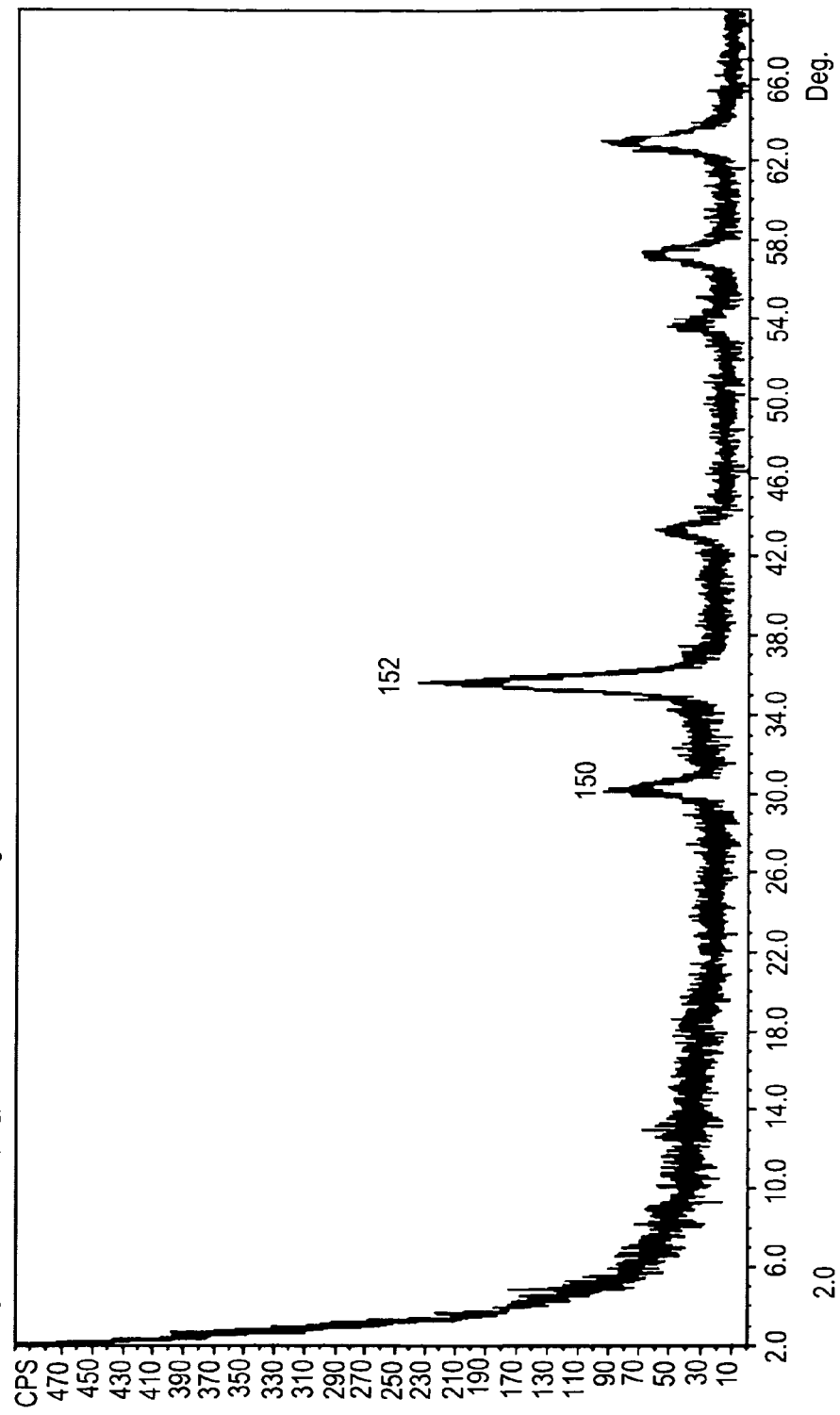

FIGS. 14A and 14B show the results of X-ray diffraction (XRD) experiments performed to characterize the stability of ferromagnetic $Fe_3O_4$ (magnetite) particles in a fluorocarbon-based ferrofluid. The ferrofluid was subjected to a water and oxygen environment at room temperature. XRD (Scintag XDS2000) was performed after an exposure of day (FIG. 14A). 1 week, 1 month, and 8 weeks (FIG. 14B), to study the performance, integrity, and durability of the ferrofluid. 2θ XRD peaks obtained from the X-ray diffractogram were correlated using International Center for Diffraction Data and crystal structure to identify the composition of the ferrofluid. In addition, the ferrofluid was assessed under an optical microscope throughout the course of the experiment to evaluate its integrity.

2θ XRD peaks taken after 8 weeks of exposure to water and oxygen (e.g., the peaks at approximately 30° (peak 150) and 35.5° (peak 152)) are characteristic of magnetite ($Fe_3O_4$), suggesting that the ferrofluid is chemically stable and that exposure to water and oxygen does not have an oxidative effect on the nanoparticles. Similar results (not shown) were also obtained after 3 months of exposure of the ferrofluid to water and oxygen.

The interaction between the ferrofluid and the glass capillary was assessed with contact angle and adhesion measurements. A computer-controlled CCD camera (Sony XCD-V50) with green light emitting diode (LED) background illumination was used to measure the contact angle of ferrofluid droplets on glass slides with hydrophilic or hydrophobic coatings in order to assess the surface interaction between the glass and the ferrofluid. The glass slides were silanized with a perfluorosilane (hydrophobic) or a PEG-silane (hydrophilic). One glass slide was left uncoated as a control. All slides were thoroughly cleaned by rinsing them several times with ethanol and water and blown dry with compressed filtered air.

Contact angle measurements were obtained at both air and water interfaces using a custom-made glass cuvette. The contact angle of the ferrofluid in air was $\phi_{air} \approx 25°$ for uncoated glass, $\phi_{air} \approx 13°$ for PEG-silane coated (hydrophilic) glass, and $\phi_{air} \approx 19°$ for fluorosilane coated (hydrophobic) glass. The contact angle measurements in water showed a larger difference between contact angles of the ferrofluid on the different surfaces. The contact angle of the ferrofluid in water was $\phi_{water} \approx 52°$ for uncoated glass, $\phi_{water} \approx 48$ for PEG-silane coated (hydrophilic) glass, and $\phi_{water} \approx 32$ for fluorosilane coated (hydrophobic) glass.

As a control, the contact angle of water on each of the glass surfaces was also measured. The contact angle of water in air was $\phi_{air} \approx 20°$ for uncoated glass, $\phi_{air} \approx 37°$ for PEG-silane coated (hydrophilic) glass, and $\phi_{air} \approx 104°$ for fluorosilane coated (hydrophobic) glass, suggesting that the uncoated glass is more hydrophilic than the PEG-silane coated glass.

These results suggest that the ferrofluid interacts least with hydrophilic surfaces, and indicates that hydrophilic surfaces may provide good performance in a ferrofluid-based valve.

The adhesion of the ferrofluid to the various glass slides was probed using a jet of pressurized air in an attempt to blow away the ferrofluid droplet from the slide. The results were optically captured as remaining deposits of ferrofluid on the slides. This qualitative assessment provided insights into the surface interaction between the ferrofluid and the various coatings. The fluorosilane coated glass exhibited the highest adhesive interaction with the ferrofluid, followed by the PEG-silane coated glass, with the uncoated glass showing the least interaction. The samples with the least interaction provided better ferrofluid adhesion under high flow rates, smoother bending of the ferrofluid under pressure, and less break-up of the ferrofluid in the event of micro air bubbles flowing through the capillary. These behaviors can contribute to reducing the gradual loss of ferrofluid material from the valve.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A device for controlling fluid flow, comprising:
a tube configured to receive fluid from a fluid source; and
a valve for controlling fluid flow through the tube, wherein the valve is responsive to a fluid pressure in the tube and comprises:
a first magnet disposed outside the tube and at a fixed first distance from the tube;
a second magnet disposed outside the tube substantially opposite the first magnet and at a second distance from the tube, wherein the second distance is greater than the first distance; and
a ferromagnetic fluid disposed within the tube between the first magnet and the second magnet and held in position by a magnetic field generated by at least the first magnet, wherein the ferromagnetic fluid is present in an amount sufficient to seal the tube when the fluid pressure is below a threshold pressure set by the second distance between the second magnet and the tube.

2. The device of claim 1, wherein the tube is configured to receive fluid from an eye of a patient.

3. The device of claim 1, wherein the valve is configured to open when the fluid pressure in the tube increases beyond an opening threshold fluid pressure.

4. The device of claim 3, wherein the opening threshold fluid pressure is a pressure sufficient to overcome a strength of a magnetic field generated by one or both of the first magnet and the second magnet.

5. The device of claim 1, wherein the valve is configured to close when the fluid pressure in the tube decreases below a closing threshold fluid pressure.

6. The device of claim 1, wherein the second magnet is disposed at a fixed second distance from the tube.

7. The device of claim 1, wherein the valve further includes a channel disposed between the second magnet and the tube, and wherein the width of the channel is adjustable.

8. The device of claim 1, wherein the second magnet is an electromagnet.

9. The device of claim 1, wherein the tube includes:
a first region formed of a flexible material and configured to receive the fluid from the eye; and
a second region adjacent to the first region and formed of a rigid material, wherein the valve is disposed in the rigid region of the tube.

10. The device of claim 1, wherein the first magnet is in contact with the tube.

11. The device of claim 1, wherein the ferromagnetic fluid includes ferromagnetic particles disposed in a carrier fluid, wherein the carrier fluid is immiscible with water.

12. The device of claim 1, wherein the ferromagnetic fluid is contained within a membrane.

13. The device of claim 1, wherein a separation between the first magnet and the tube is less than a separation between the second magnet and the tube.

14. A method for controlling fluid flow, the method comprising:
receiving fluid from a fluid source into a tube; and
controlling fluid flow through the tube using a valve responsive to a fluid pressure in the tube, the valve including a ferromagnetic fluid disposed within the tube between a first magnet and a second magnet and held in position by a magnetic field generated by at least the first magnet.

15. The method of claim 14, wherein receiving fluid includes receiving fluid from an eye of a patient into the tube.

16. The method of claim 14, wherein controlling fluid flow includes causing the valve to close when the fluid pressure in the tube is less than a threshold fluid pressure.

17. The method of claim 16, wherein when the fluid pressure in the tube is less than the threshold fluid pressure, a strength of a magnetic field generated by the second magnet is sufficient to hold the ferromagnetic fluid in a position that blocks fluid flow through the tube.

18. The method of claim 14, wherein controlling fluid flow includes causing the valve to open when the pressure difference increases beyond an opening threshold pressure difference.

19. The method of claim 14, wherein controlling fluid flow includes causing the valve to open when the fluid pressure in the tube increases beyond an opening threshold fluid pressure.

20. The method of claim 19, wherein the opening threshold pressure difference is a pressure sufficient to overcome a strength of a magnetic field generated by the second magnet.

21. The method of claim 14, wherein controlling fluid flow includes causing the valve to close when the pressure difference decreases beyond a closing threshold fluid pressure.

22. The method of claim 14, wherein controlling fluid flow includes adjusting a distance between the second magnet and the tube.

23. The method of claim 14, wherein the second magnet is an electromagnet, and wherein controlling fluid flow includes adjusting a strength of the electromagnet.

24. A device for controlling fluid flow, comprising:
a tube configured to receive fluid from a fluid source; and
a valve, disposed along the tube, for controlling fluid flow through the tube, wherein the valve is responsive to a fluid pressure in the tube and comprises:
a valve member including ferromagnetic particles, and
a magnet disposed outside the tube and configured to apply a magnetic field to the valve member,
wherein the valve member is held in a configuration that seals the tube by the magnetic field generated by the magnet when the fluid pressure is below a threshold pressure, and
wherein the valve member is configured to open when the fluid pressure exceeds the threshold pressure, the threshold pressure being sufficient to overcome a strength of the magnetic field generated by the magnet.

25. The device of claim 24, wherein the valve is disposed at an end of the tube.

26. The device of claim 24, wherein the valve member includes a membrane and a ferromagnetic fluid contained within the membrane.

27. The device of claim 24, wherein the valve member includes a membrane at least partially coated in a layer of ferromagnetic particles.

28. The device of claim 24, wherein the valve member includes a membrane and magnetic nanoparticles homogeneously distributed across the area and through the thickness of the membrane.

29. A method for treating glaucoma, the method comprising:
positioning a device in an eye of subject diagnosed with glaucoma, the device including:
a tube configured to receive fluid from the eye, and
a valve responsive to a fluid pressure in the tube, wherein the fluid pressure in the tube is related to a fluid pressure in the eye, and wherein the valve includes a ferromagnetic fluid disposed within the tube between a first magnet and a second magnet and held in position by a magnetic field generated by at least the first magnet; and regulating the fluid pressure in the eye by controlling fluid flow through the tube using the valve.

30. The method of claim 29, wherein controlling fluid flow through the tube comprises causing the valve to close when the fluid pressure in the tube is less than a threshold fluid pressure.

31. The method of claim 29, wherein controlling fluid flow through the tube comprises causing the valve to close when a difference between the fluid pressure in the tube and the fluid pressure in the eye decreases beyond a closing threshold fluid pressure.

32. The method of claim 29, wherein controlling fluid flow through the tube comprises causing the valve to open when the fluid pressure in the tube increases beyond an opening threshold fluid pressure.

33. The method of claim 29, wherein controlling fluid flow through the tube comprises causing the valve to open when a difference between the fluid pressure in the tube and the fluid pressure in the eye increases beyond an opening threshold fluid pressure.

34. The method of claim 33, wherein the opening threshold fluid pressure is a pressure sufficient to overcome a strength of a magnetic field generated by the second magnet.

* * * * *